(12) United States Patent
Gaschino et al.

(10) Patent No.: US 9,114,010 B2
(45) Date of Patent: Aug. 25, 2015

(54) KIT FOR THE MANIPULATION OF IMPLANTABLE MEDICAL DEVICES

(71) Applicant: Sorin Group Italia S.r.l., Milan (IT)

(72) Inventors: Paolo Gaschino, Castagneto Po (IT); Andrea Mariotto, Turin (IT); Giovanni Rolando, Chivasso (IT); Massimiliano Ares, Collegno (IT)

(73) Assignee: Sorin Group Italia S.r.l., Milan (IT)

( * ) Notice: Subject to any disclaimer, the term of this patent is extended or adjusted under 35 U.S.C. 154(b) by 321 days.

(21) Appl. No.: 13/849,461

(22) Filed: Mar. 22, 2013

(65) Prior Publication Data

US 2013/0261742 A1 Oct. 3, 2013

(30) Foreign Application Priority Data

Mar. 28, 2012 (EP) .................................... 12425064

(51) Int. Cl.
*A61F 2/24* (2006.01)
*A61F 2/00* (2006.01)
*A61F 2/95* (2013.01)

(52) U.S. Cl.
CPC ............. *A61F 2/2427* (2013.01); *A61F 2/0095* (2013.01); *A61F 2/2412* (2013.01); *A61F 2002/9522* (2013.01)

(58) Field of Classification Search
CPC ... A61F 2/0095; A61F 2/2427; A61F 2/2412; A61F 2/24; A61F 2/2409; A61F 2/2418; A61F 2/2439; A61F 2/2403; A61F 2/2466; A61F 2002/9522
See application file for complete search history.

(56) References Cited

U.S. PATENT DOCUMENTS

| | | |
|---|---|---|
| 2009/0054976 A1 | 2/2009 | Tuval et al. |
| 2010/0049313 A1 | 2/2010 | Alon et al. |
| 2010/0252470 A1 | 10/2010 | Ryan et al. |

FOREIGN PATENT DOCUMENTS

| | | |
|---|---|---|
| EP | 2014257 B1 | 8/2010 |
| WO | WO2008008365 A2 | 2/2008 |

(Continued)

OTHER PUBLICATIONS

International Search Report issued in PCT/IB2013/052074, mailed Jul. 17, 2013, 6 pgs. (SR_PCT052074).

(Continued)

*Primary Examiner* — Jocelin Tanner
(74) *Attorney, Agent, or Firm* — Faegre Baker Daniels LLP

(57) ABSTRACT

A kit for facilitating crimping of a prosthetic heart valve for implantation at an aortic valve site in a human heart, the aortic valve site including a plurality of valve sinuses, the kit comprising a prosthetic aortic heart valve having a tubular structure and a first central axis including an anchoring structure comprising an annular outflow member, an annular inflow member, and a plurality of axial connection formations arranged in pairs angularly distributed around the central axis, and a plurality of leaflets coupled to the anchoring structure and adapted to substantially allow blood flow in a first direction and to substantially prevent blood flow in a second direction. The kit further includes a holder member comprising a first disc support member that includes a central hub and a plurality of bridge elements, wherein the hub and the bridge elements extend axially from opposite sides of the disc support member; and a second ring support member that includes receptacles for coupling with the bridge elements, and a plurality of finger formations protruding axially from the ring member and extending lengthwise along at least a portion of the prosthetic aortic heart valve.

16 Claims, 16 Drawing Sheets

(56) References Cited

FOREIGN PATENT DOCUMENTS

| WO | WO2009091509 A1 | 7/2009 |
| WO | WO2009108942 A1 | 9/2009 |
| WO | WO2010130789 A1 | 11/2010 |

OTHER PUBLICATIONS

Partial European Search Report issued in EP12425064, mailed Aug. 28, 2012, 14 pgs. (SR_EPPartial12425064).

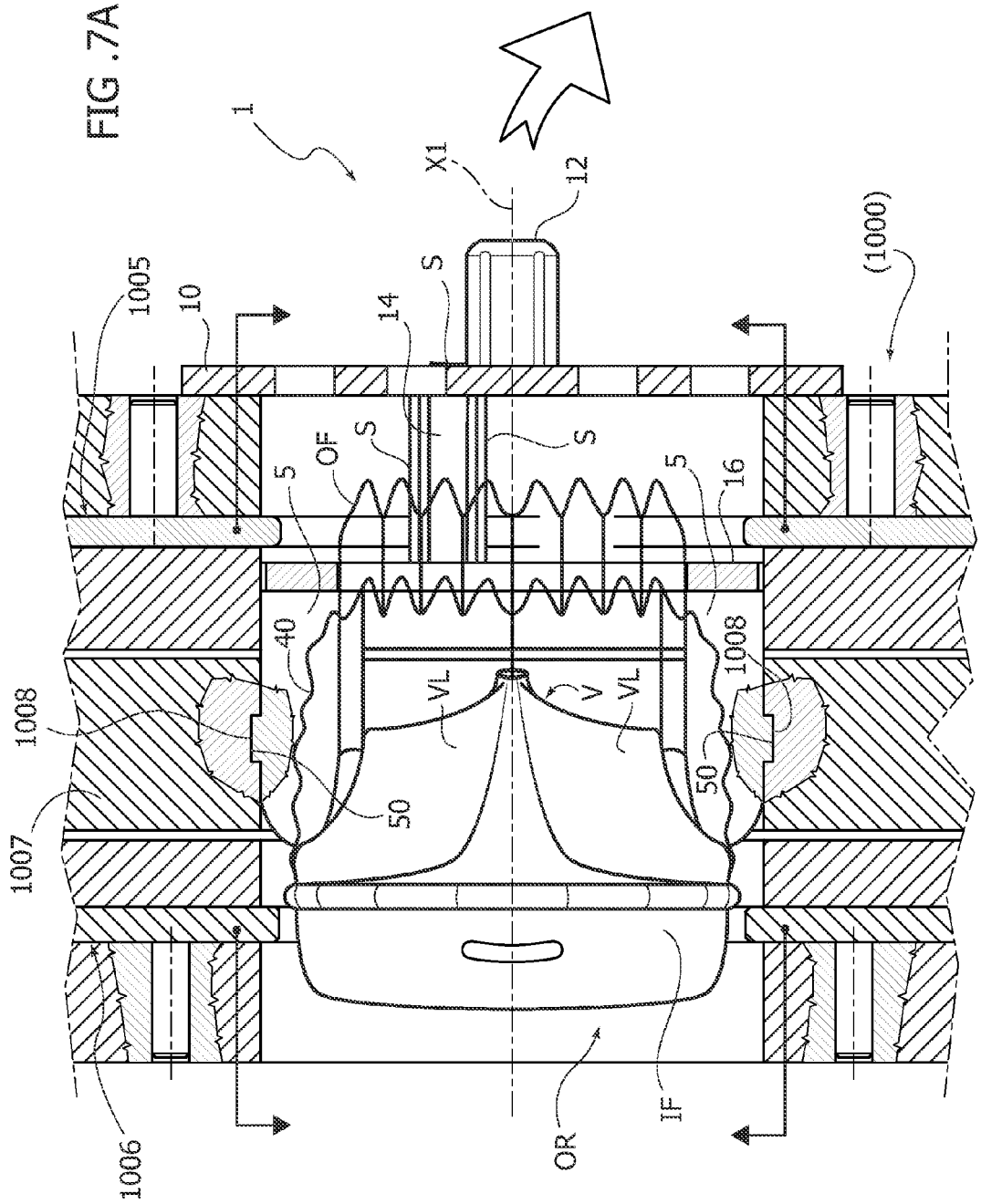

KIT FOR THE MANIPULATION OF IMPLANTABLE MEDICAL DEVICES

CROSS-REFERENCE TO RELATED APPLICATION

This application claims priority to European Application No. 12425064.8, filed Mar. 28, 2012, which is herein incorporated by reference in its entirety.

TECHNICAL FIELD

This invention relates to a kit for manipulating implantable medical devices such as, e.g., heart valve prostheses during a pre-operative procedure preceding the implantation of such devices.

BACKGROUND

In the fields of heart valve surgery and interventional cardiology, easy handling of medical devices and the reduction of the time required to perform a surgical intervention and procedure are main topics of the medical and technological research in the field. With reference to the implantation of expandable heart valve prostheses (such as, e.g., sutureless valve prostheses), a current practice provides that a heart valve prosthesis should be stored in a sterile environment in order to maintain its integrity and also in order to prevent air from being trapped in the structure of the prosthesis. Such prostheses may also be required to be crimped (i.e., radially collapsed) and coupled to a delivery instrument in order to be delivered to an implantation site, for example, in a minimally invasive or percutaneous procedure.

Crimping an implantable medical device may present a number of important issues. While many crimping devices with different features have been devised to facilitate the crimping operation, such a step may remain rather delicate and complex to perform. One of the challenges for the practitioner when crimping an implantable medical device onto a delivery instrument lies in achieving a desired positioning, in particular, an angular positioning, of the implantable device on the crimping device. In various prior art devices, the delivery instruments are provided with angular indicia (for example, markers which are intended to identify the commissures of an aortic or tricuspid valve) intended to aid the practitioner in correctly positioning the implantable device at the implantation site. These devices, however, may involve a risk of damaging the implantable medical device as the practitioner adjusts the angular position of the implantable medical device within the crimping orifice by contacting and manipulating the implantable device directly.

SUMMARY

In various embodiments, the present invention provides means which render manipulation of implantable medical devices easier, safer, faster and more accurate in comparison to previously-known devices.

Various embodiments of the invention provide a kit and/or a crimping apparatus having the features forming the subject of the appended claims, which form an integral part of the technical disclosure herein provided in relation to the invention. In various embodiments, a kit may include: an implantable medical device having a tubular structure and a central axis, the implantable medical device including at least one axial portion radially contractible towards the central axis to permit crimping of the implantable medical device, and a holder member supporting the implantable medical device from outside the tubular structure thereof, the holder member extending axially of the tubular structure of the implantable medical device and at least in part axially clear of said at least one axial portion to permit unimpeded radial contraction of said at least one axial portion.

Certain embodiments may provide a crimping apparatus for crimping an implantable medical device, the apparatus including: a radially contractible crimping opening to receive at least one radially contractible axial portion of the implantable medical device supported by a holder member, whereby a radial contraction of said crimping opening produces radial contraction of said at least one radially contractible axial portion of the device, angular indicia provided on at least one of the crimping apparatus and the holder member to permit rotating the holder member supporting the implantable medical device to a given angular position with respect to the crimping opening of the crimping apparatus.

Exemplary embodiments of the invention include:

Embodiment 1

A kit for facilitating crimping of a prosthetic heart valve for implantation at an aortic valve site in a human heart, the aortic valve site including a plurality of valve sinuses, the kit comprising: a prosthetic aortic heart valve having a tubular structure and a first central axis including: an anchoring structure comprising an annular outflow member, an annular inflow member, and a plurality of axial connection formations that connect the annular outflow member and the annular inflow member, wherein the axial connection formations are arranged in pairs angularly distributed around the central axis, and the axial connection formations bulge outward to provide anchoring at the valve site; a plurality of leaflets coupled to the anchoring structure and adapted to substantially allow blood flow in a first direction and to substantially prevent blood flow in a second direction; wherein the annular outflow member and the annular inflow member are radially contractible toward the central axis; a holder member supporting the prosthetic aortic heart valve, the holder member comprising: a first disc support member that includes a central hub and a plurality of bridge elements, wherein the hub and the bridge elements extend axially from opposite sides of the disc support member; and a second ring support member that includes receptacles for coupling with the bridge elements, and a plurality of finger formations protruding axially from the ring member and extending lengthwise along at least a portion of the prosthetic aortic heart valve, wherein the ring member surrounds the prosthetic aortic heart valve and is axially aligned at or slightly proximal to the annular outflow portion, wherein the plurality of finger formations are circumferentially spaced and sized to fit between the angularly distributed pairs of axial connection formations such that each pair of axial connection formations frictionally engages and thereby couples to a corresponding finger formation, and wherein the first disc support member and the second ring support member are releasably coupled by sutures.

Embodiment 2

The kit of embodiment 1, further comprising a container holding a liquid and having a cap, the container sized and shaped to hold the prosthetic aortic heart valve and the holder member such that the valve is immersed in the liquid and the hub of the holder member is connected to or integral with the cap.

Embodiment 3

The kit of embodiment 1 or 2, wherein the holder member includes a plurality of angular indicia to facilitate the holder member to be placed in a desired angular position with respect to a crimping opening of a crimping apparatus used to crimp the prosthetic aortic heart valve.

Embodiment 4

The kit of any of embodiments 1-3, wherein the prosthetic aortic heart valve includes an elastically biased tubular structure resisting radial contraction, and wherein the holder member supports the prosthetic aortic heart valve by radially constraining said elastically biased tubular structure.

Embodiment 5

A kit for facilitating crimping of a prosthetic heart valve for implantation at an aortic valve site in a human heart, the aortic valve site including a plurality of valve sinuses, the kit comprising: a prosthetic aortic heart valve having a tubular structure and a first central axis including: an anchoring structure comprising an annular outflow member, an annular inflow member, and a plurality of axial connection formations that connect the annular outflow member and the annular inflow member, wherein the axial connection formations are arranged in pairs angularly distributed around the central axis, and the axial connection formations bulge outward to provide anchoring at the valve site; a plurality of leaflets coupled to the anchoring structure and adapted to substantially allow blood flow in a first direction and to substantially prevent blood flow in a second direction; wherein the annular outflow member and the annular inflow member are radially contractible toward the central axis to permit crimping; a holder member supporting the prosthetic aortic heart valve, the holder member comprising: a first disc support member that includes a central hub and a plurality of bridge elements, wherein the hub and the bridge elements extend axially from opposite sides of the disc support member; and a second ring support member that includes receptacles for coupling with the bridge elements, and a plurality of finger formations protruding axially from the ring member and extending lengthwise along at least a portion of the prosthetic aortic heart valve, wherein the first disc support member and the second ring support member are releasably coupled.

Embodiment 6

The kit of embodiment 5, further comprising a container holding a liquid and having a cap, the container sized and shaped to hold the prosthetic aortic heart valve and the holder member such that the valve is immersed in the liquid and the hub of the holder member is connected to or integral with the cap.

Embodiment 7

The kit of embodiment 5 or 6, wherein the prosthetic aortic heart valve includes an elastically biased tubular structure resisting radial contraction, wherein said holder member supports the prosthetic aortic heart valve by radially constraining said elastically biased tubular structure.

Embodiment 8

The kit of any of embodiments 5-7, wherein the first and second support members of the holder member are releasably coupled by sutures.

Embodiment 9

The kit of any of embodiments 5-8, wherein the axial connection formations are arranged in angularly spaced pairs and the finger formations are sized and dimensioned to fit between the angularly spaced pairs of axial connection formations, such that the finger formations releasably couple to the axial connection formations.

Embodiment 10

The kit of any of embodiments 5-9, wherein the holder member includes angular indicia provided thereon in order for the holder member to be placed in a desired angular position with respect to a crimping opening of a crimping apparatus used to crimp the prosthetic aortic heart valve.

Embodiment 11

The kit of any of embodiments 5-10, wherein the second ring support member surrounds and supports the annular outflow portion of the prosthetic aortic heart valve.

Embodiment 12

The kit of any of embodiments 5-11, wherein the finger formations of the second ring support member extend axially a sufficient distance to surround and support the annular inflow portion of the prosthetic aortic heart valve.

Embodiment 13

The kit of any of embodiments 5-12, further comprising a crimping apparatus for crimping the prosthetic aortic heart valve, the crimping apparatus including a radially contractible crimping opening configured for receiving at least one radially contractible axial portion of the prosthetic aortic heart valve coupled to the holder, whereby a radial contraction of said crimping opening produces radial contraction of said at least one radially contractible axial portion of the prosthetic aortic heart valve.

Embodiment 14

The kit of any of embodiments 5-13 further comprising angular indicia provided on at least one of the crimping apparatus and the holder member to permit rotating the holder member supporting the prosthetic aortic heart valve to a given angular position with respect to the crimping opening of the crimping apparatus.

Embodiment 15

The kit of any of embodiments 5-14, wherein the finger formations of the holder include a first engagement feature adapted to couple with a second engagement feature on the crimping apparatus, such that the holder member is retained at a given angular position within the crimping apparatus.

Embodiment 16

A method of crimping a prosthetic aortic heart valve, the method comprising the steps of: providing a crimping apparatus comprising a first annular body and a second annular body arranged for relative rotation generally about an axis, an array of linear crimping elements having first ends coupled to the second annular body, wherein the first body and the second body are configured to rotate about the axis between a first position, wherein the crimping elements define a first diameter orifice, and a second position, wherein the crimping elements define a second diameter orifice; and providing a kit comprising: a prosthetic aortic heart valve having a tubular structure and a first central axis including: an anchoring structure comprising an annular outflow member, an annular inflow member, and a plurality of axial connection formations that connect the annular outflow member and the annular inflow member, wherein the axial connection formations are arranged in pairs angularly distributed around the central axis, and the axial connection formations bulge outward to provide anchoring at the valve site; a plurality of leaflets coupled to the anchoring structure and adapted to substantially allow blood flow in a first direction and to substantially prevent blood flow in a second direction; wherein the annular outflow member and the annular inflow member are radially contractible toward the central axis to permit crimping; a holder member supporting the prosthetic aortic heart valve, the holder member comprising: a first disc support member that includes a central hub and a plurality of bridge elements, wherein the hub and the bridge elements extend axially from opposite sides of the disc support member; and a second ring support member that includes receptacles for coupling with the bridge elements, and a plurality of finger formations protruding axially from the ring member and extending lengthwise along at least a portion of the prosthetic aortic heart valve, wherein the finger formations include a first engagement feature for coupling with a second engagement feature on the crimping apparatus, and wherein the first disc support member and the second ring support member are releasably coupled; axially advancing the holder into the first diameter orifice such that; rotating the holder until the first and second engagement features engage; cutting the sutures coupling the first disc support member and the second ring support member; removing the first disc support member from the crimping apparatus; axially advancing a delivery device through the second ring support member and into first diameter orifice of the crimping apparatus; rotating the first annular body and second annular body of the crimping apparatus to the second position in order to crimp the annular inflow portion and the annular outflow portion of the prosthetic heart valve; and coupling at least one of the crimped annular inflow portion and the crimped annular outflow portion onto the delivery device.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

Various embodiments will now be described with reference to the attached figures, provided purely by way of non-limiting example, and wherein:

FIG. 7A is a cross-sectional view of a cross-section taken along axis X1 of FIG. 7 showing a stage of the exemplary operative sequence of FIGS. 5, 6, 7, and 8;

Figure 1:
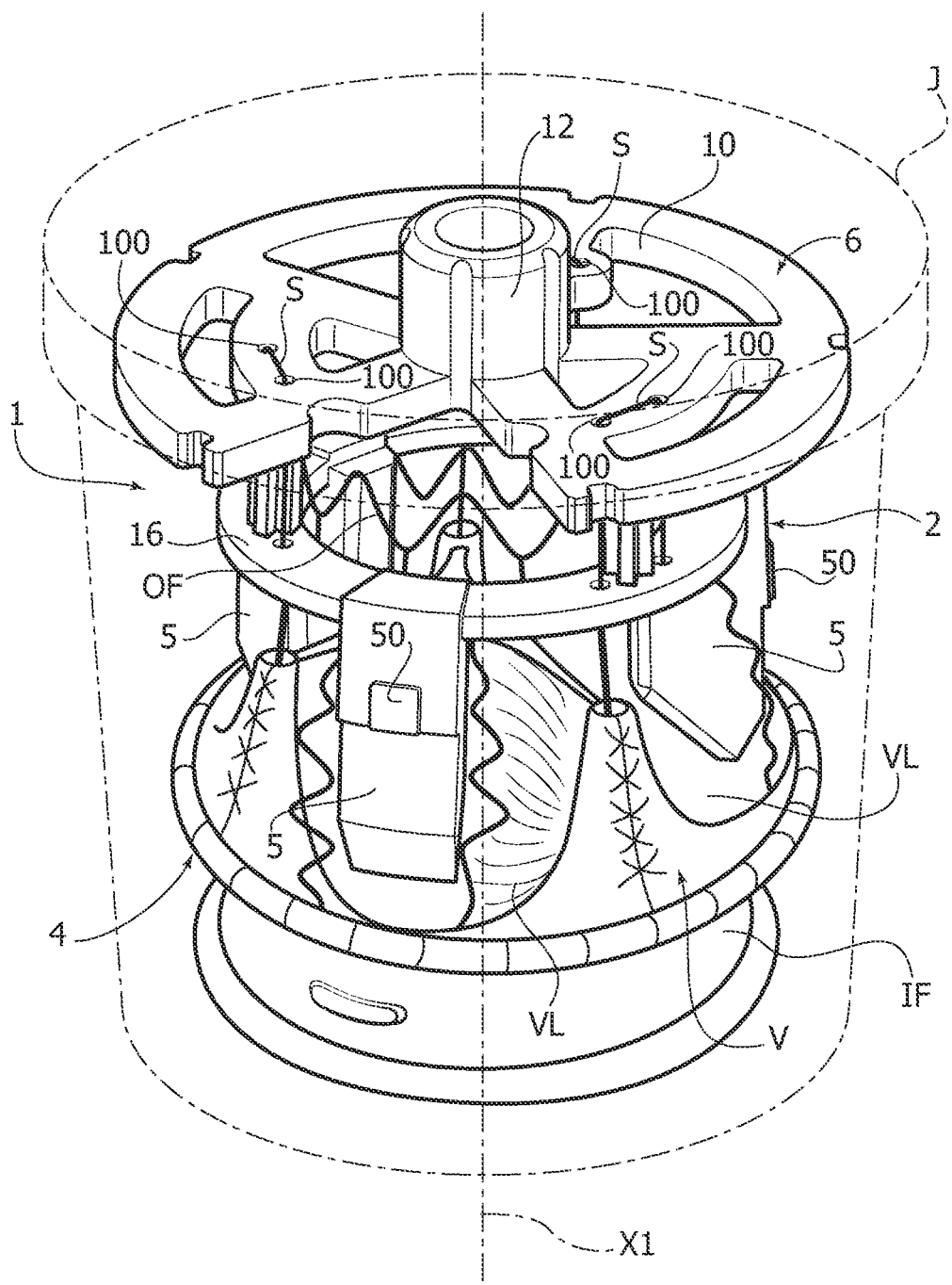
FIG. 1 is a perspective view of a kit according to various embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following description, numerous specific details are given to provide a thorough understanding of various exemplary embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the embodiments.

The reference number 1 in the figures designates, as a whole, a kit according to various embodiments. As shown in FIG. 1, for example, the kit 1 includes a holder member 2 and an implantable medical device 4. As exemplary of such an implantable medical device 4, the figures (e.g., FIG. 1A) show a heart valve prosthesis such as disclosed in, e.g., EP-A-1 690 515, which is hereby incorporated by reference in its entirety. Those of skill in the art will appreciate that the disclosure is not limited to heart valve prostheses and, more to the point, to such an exemplary heart valve.

In various embodiments, an implantable medical device 4 may be coupled to the holder member 2 in a manner that will be described more in detail in the following description. The holder member 2 may have a cage-like structure including a plurality of finger formations 5, which are adapted to extend lengthwise of the implantable medical device 4. The finger formations 5 may be angularly spaced about 120 degrees apart about a circumference of the holder member 2. In various embodiments, the holder member 2 may be releasably coupled to a support member 6. Further details of exemplary embodiments will be provided in the following description.

Figure 3:
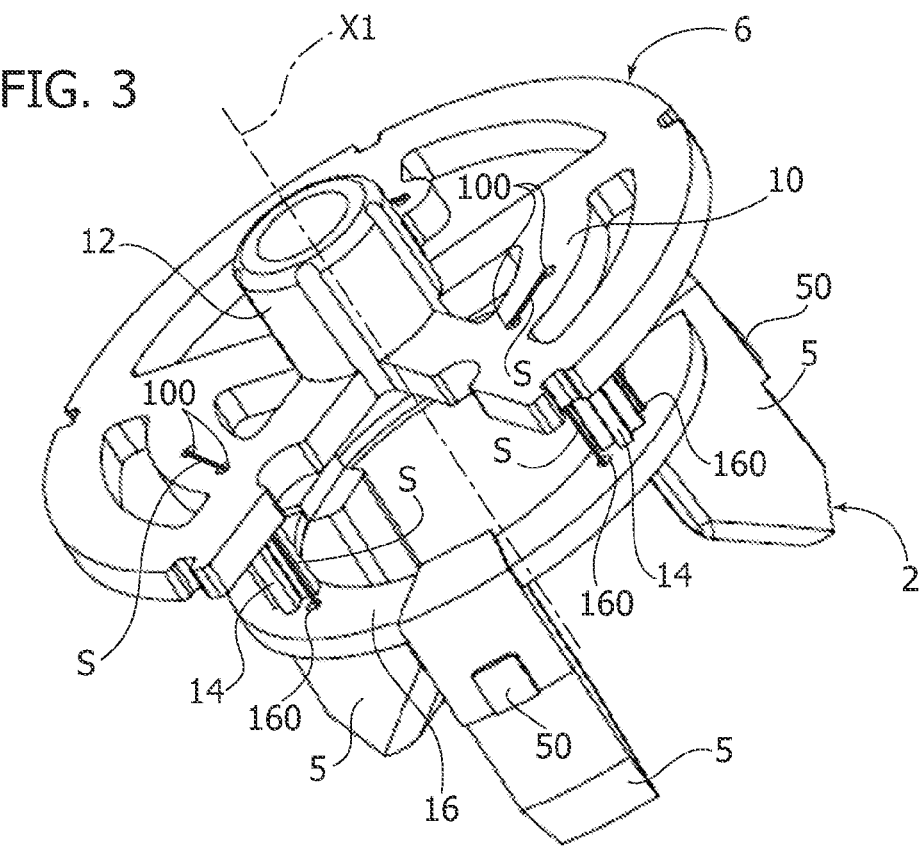
FIG. 3 is a perspective view of a kit according to various embodiments with some components removed for the sake of clarity.
Figure 4:
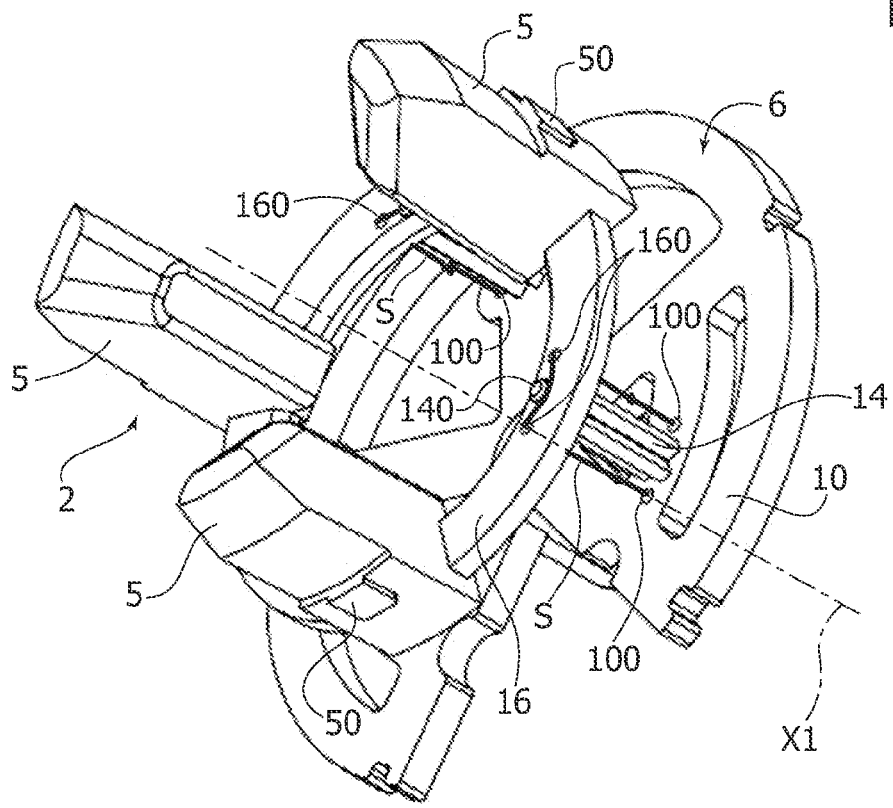
FIG. 4 is a perspective view corresponding to that of FIG. 3 but taken from a different angle.

As shown in FIGS. 3 and 4, in various exemplary embodiments, the support member 6 may include a disc-shaped member 10, a hub 12 coaxial to the disc-shaped member 10 and integral therewith and a plurality of bridge elements 14, integral with the disc-shaped member 10 and lying on an opposite side with respect to the hub 12. In exemplary embodiments, the bridge elements 14 extend orthogonally from the disc-shaped member 10. In various embodiments, the disc-shaped member 10 may include a number of holes, openings, apertures, or cutaways.

In various embodiments, the holder member 2 may include a ring member 16 from which the finger formations 5 protrude axially. In an exemplary embodiment, the holder member 2 may be coupled with the support member 6 by means of the bridge elements 14, which engage corresponding receptacles provided on the ring member 16. Such receptacles may include, for example, through holes 100, 160 sized and dimensioned to receive reference pins 140 of each bridge element 14.

A plurality of through holes 100, 160 may be provided, on the disc-shaped member 10 and on the ring member 16, respectively. In an exemplary embodiment, the through holes 100, 160 may be arranged in pairs astride of the bridge elements 14 and the receptacles for the bridge elements 14 on the ring member 16. At each bridge element 14 (three in the exemplary embodiment shown) a quadrangular pattern of through holes may be provided including a pair of through holes 100 and a pair of through holes 160, all located at positions corresponding to the vertices of a rectangular shape. In other words, corresponding through holes 100 and 160 are axially aligned.

A wire member, such as, e.g., a suture thread S, may be passed through the holes 100, 160 in order to form a loop substantially copying the shape of the quadrangular pattern of the holes 100, 160, e.g., due to the fact that the suture wire is slightly tensioned. The suture thread S is an example of a means to secure the support member 6 to the holder member 2, thereby rendering them temporarily coupled. In embodiments, such as those depicted in FIGS. 3, 4, the holder member 2 may be coupled to the supporting portion 6 by means of three sets of suture threads S, each associated with a finger formation 5.

In certain embodiments, the holder member 2 may be provided integral with the support member 6. Releasable coupling may then be achieved by means of yieldable connection portions, i.e., being configured to be torn apart under, e.g., shear stresses and/or axial stresses above a predetermined value. Alternative coupling systems may include snap fit, interference fit, or other interlocking structures. Further details of exemplary embodiments will be provided in the following description.

Furthermore, in various embodiments each finger formation 5 may be provided with an angular indicia 50, in the form, e.g., of a relief provided on an external axial surface of each finger formation 5. In various embodiments, each finger formation 5 may have a free end (i.e., an end which is opposite to the end integral with the ring member 16) having a chamfered shape for reasons which will be evident in the description that follows. In certain embodiments, the external axial surface of each finger formation 5 may be generally cylindrical so that the chamfered shape of the free end assumes the features typical of a conical surface.

Figure 2:
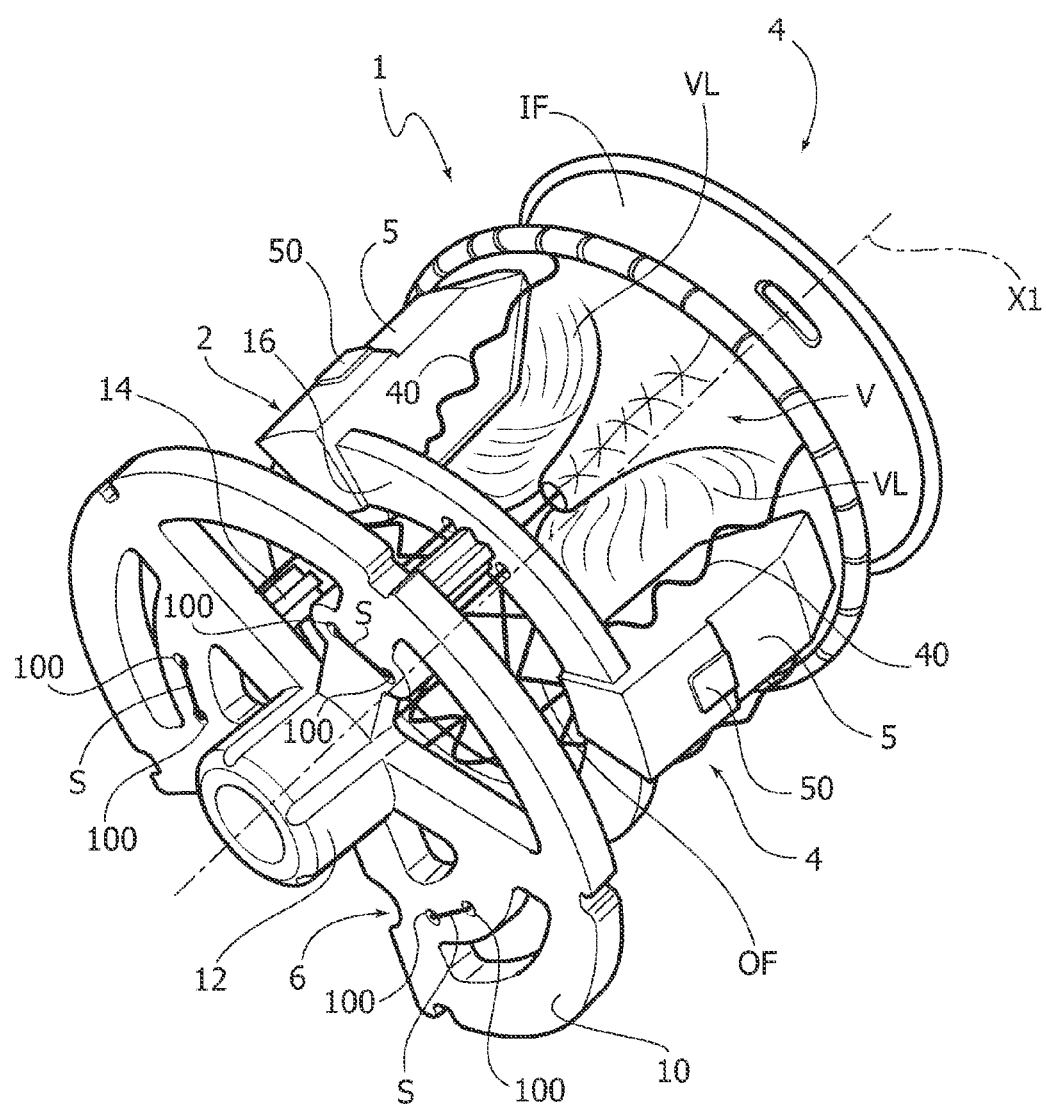
FIG. 2 is a perspective view corresponding to that of FIG. 1 but taken from a different angle.

FIGS. 1 and 2 illustrate an exemplary combination of an implantable medical device 4, a holder member 2, and a support member 6, according to various embodiments. In these figures, the implantable medical device 4 is exemplified in the form of an implantable heart valve prosthesis. Examples of such a valve adapted for use with certain embodiments are various embodiments disclosed in EP-A-1 690 515 (previously mentioned) and/or EP-A-2 119 417, which are incorporated by reference herein.

In the description that follows, a number of examples of an implantable medical device will be provided for a better understanding of the embodiments of the kit described. Therefore, the terms "implantable medical device" will sometimes be replaced by terms such as "prosthesis" or "heart valve prosthesis" or the like (e.g., "valve") depending on the specific example of implantable medical device referred to in the description.

Figure 1A:
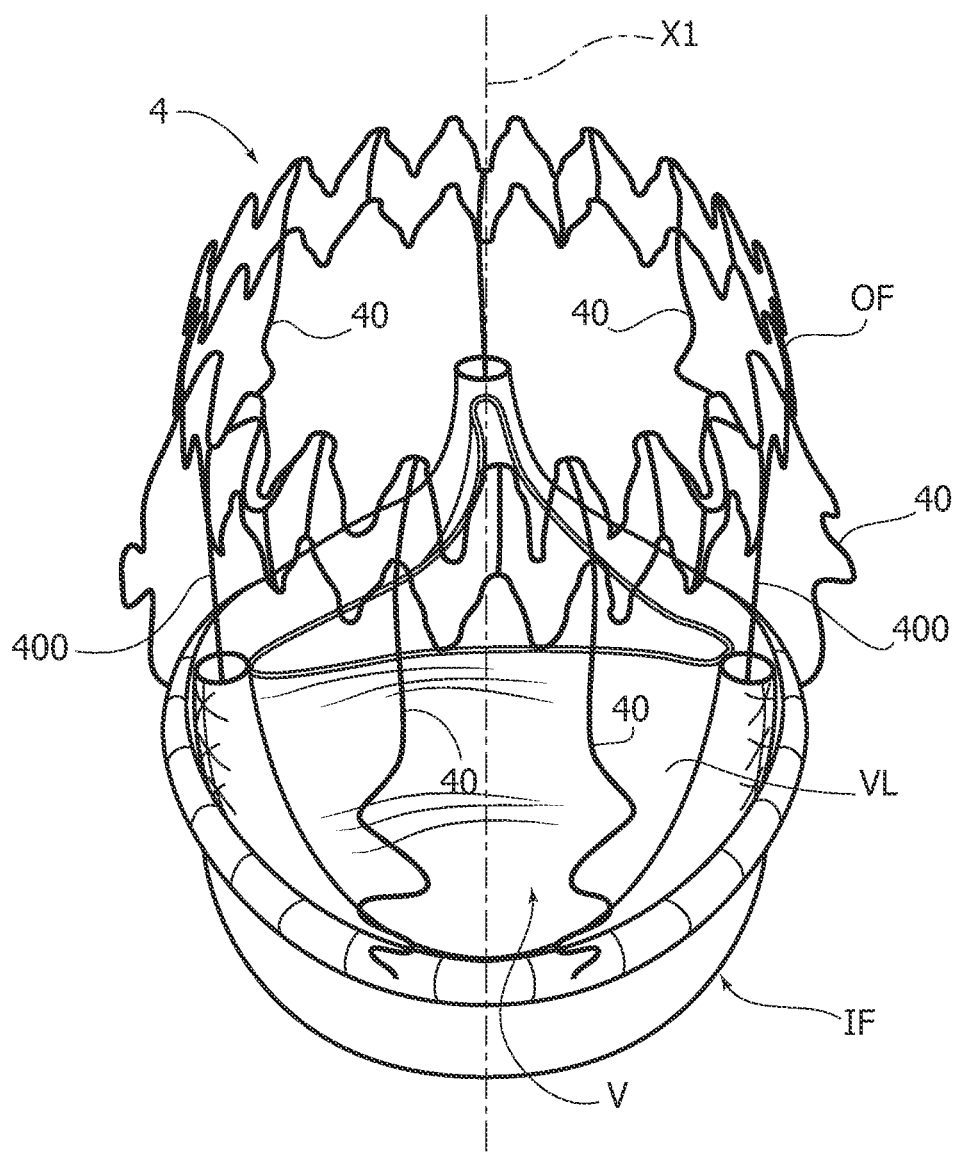
FIG. 1A is a perspective view of an exemplary implantable medical device in a kit according to various embodiments.

In various embodiments, the implantable heart valve prosthesis 4 may include a tubular structure having a central axis X1 (FIG. 1A). The implantable heart valve prosthesis 4 also includes first and second axial portions IF ("IF" for "inflow" portion), OF ("OF" for "outflow" portion), which are annular in shape and radially contractible towards the central axis X1 to permit crimping of the device 4 in order for the device to be mounted on a delivery instrument (not shown). In various embodiments, the radially contractible portions IF, OF may be connected via axial connection formations 40, which are angularly distributed around the central axis X1. In certain embodiments, the axial connection formations 40 may have a serpentine pattern. In various embodiments, the axial connection formations 40 may be adapted to bulge outwards to provide anchoring of the prosthesis at the implantation site. In exemplary embodiments, the formations 40 are arched radially outward such that they together define a diameter larger than a diameter of either of the radially contractible portions IF, OF. In exemplary embodiments, the formations 40 have the shape and configuration described in EP-A-1 690 515, which is incorporated by reference herein.

Axial formations indicated by the reference 400 (FIG. 1A) may be configured for supporting a biological prosthetic heart valve V (e.g., a porcine valve) including a plurality of coapting valve leaflets VL. In exemplary embodiments, the axial formations 400 are disposed at locations corresponding to leaflet commissures.

In the exemplary embodiments shown in the figures, the prosthesis 4 may be suitable for the replacement of a native, diseased aortic valve. The annular portions IF, OF are end portions of the prosthesis 4 and are associated, respectively, with an inflow section and an outflow section of the implantation site (the terms "inflow" and "outflow" being used with reference to the direction of blood flow through the valve). The axial connection formations 40 are arranged in three angularly equally spaced pairs each configured for engaging a corresponding Valsalva sinus at an aortic implantation site. In certain embodiments, at least one and optionally both of the portions IF, OF may exhibit a stent-like structure which facilitates the radial crimping of the prosthesis 4. In other words, in such embodiments, the prosthesis 4 may include a stent member including the annular portions IF, OF connected via the axial connection formations 40.

In certain embodiments, the implantable medical device 4 may include a single, radially contractible portion extending axially, while in other embodiments the implantable medical device may include an elastically biased tubular structure resisting radial contraction, i.e., exhibiting some degree of radial resiliency along the entire length thereof (e.g., a stent).

Coupling of prosthesis 4 to a holder member 2, according to various embodiments, will now be described, with reference again to FIGS. 1 and 2. In the exemplary embodiments considered, to facilitate coupling the prosthesis 4 with the holder member 2, the finger formations 5 may be angularly aligned with the gaps between the axial connection formations 40 of the prosthesis 4. In particular, in certain embodiments, the axial connection formations 40 may be arranged in angularly spaced pairs and the finger formations 5 are sized and dimensioned to fit between the pair of axial connection formations 40, thus being able to couple to the prosthesis 4. In one embodiment, for example, the finger formations 5 may be sized and dimensioned so that interference coupling is achieved with the axial connection formations 40, without giving rise to appreciable deformation of the axial connection formations 40.

In various embodiments, the chamfered shape of the ends of the finger formations 5 facilitates the advancement of each finger formation 5 between the axial connection formations 40. In fact, the coupling of the holder member 2 to the prosthesis 4 may be affected by axially pushing the holder member 2 towards the prosthesis 4 thereby urging the finger formations 5 between the corresponding pairs of axial connection formations 40. At the same time, the annular portion OF will be accommodated (for instance, with or without a small amount of radial contraction) within the ring member 16. In various embodiments, the ring member 16 is disposed somewhat axially below (i.e., in the direction toward or proximal the implantation site), such that the contractible annular portion OF is left completely uncovered by the ring member 16. In one exemplary embodiment, the ring member 16 is located about 0.1 to about 3 millimeters below (or proximal) the contractible annular portion OF.

In certain embodiments, no further fastening or securing means may be required because the coupling between the heart valve prosthesis 4 and the finger formations 5 may be maintained by means of interference between the finger formations 5 and the corresponding axial connection formations 40.

In certain embodiments, as shown in FIGS. 1 and 2, the prosthesis 4 and the holder member 2 may have a common central axis X1.

With reference to FIG. 1, in various embodiments, the kit 1 may be stored in a container, namely a jar J, herein represented in phantom line, which may be filled with a liquid beneficial to the biological material of the prosthetic valve V. Such liquid may include a sterile solution, a physiological solution or any other means intended to preserve the integrity of the biological valve V. In certain embodiments, the kit 1 may be shipped pre-inserted into the jar J to help preserve the integrity of the heart valve V.

FIGS. 5, 6, 7, and 8 show an exemplary embodiment of an operative sequence, which may be performed by using the kit 1. Reference number 1000 indicates, as a whole, a crimping apparatus for crimping implantable medical devices. The crimping apparatus 1000 includes a first crimping unit 1001 and a second crimping unit 1002, each including a respective actuation handle 1003, 1004 and a respective array of crimping elements 1005, 1006. The details of such device are known by those of skill in the art, thus the detailed description will not describe all details of such a crimping apparatus herein, save for a number of features described below. EP-A-2 014 257 describes a crimping apparatus in detail and is herein incorporated by reference.

Figure 5:
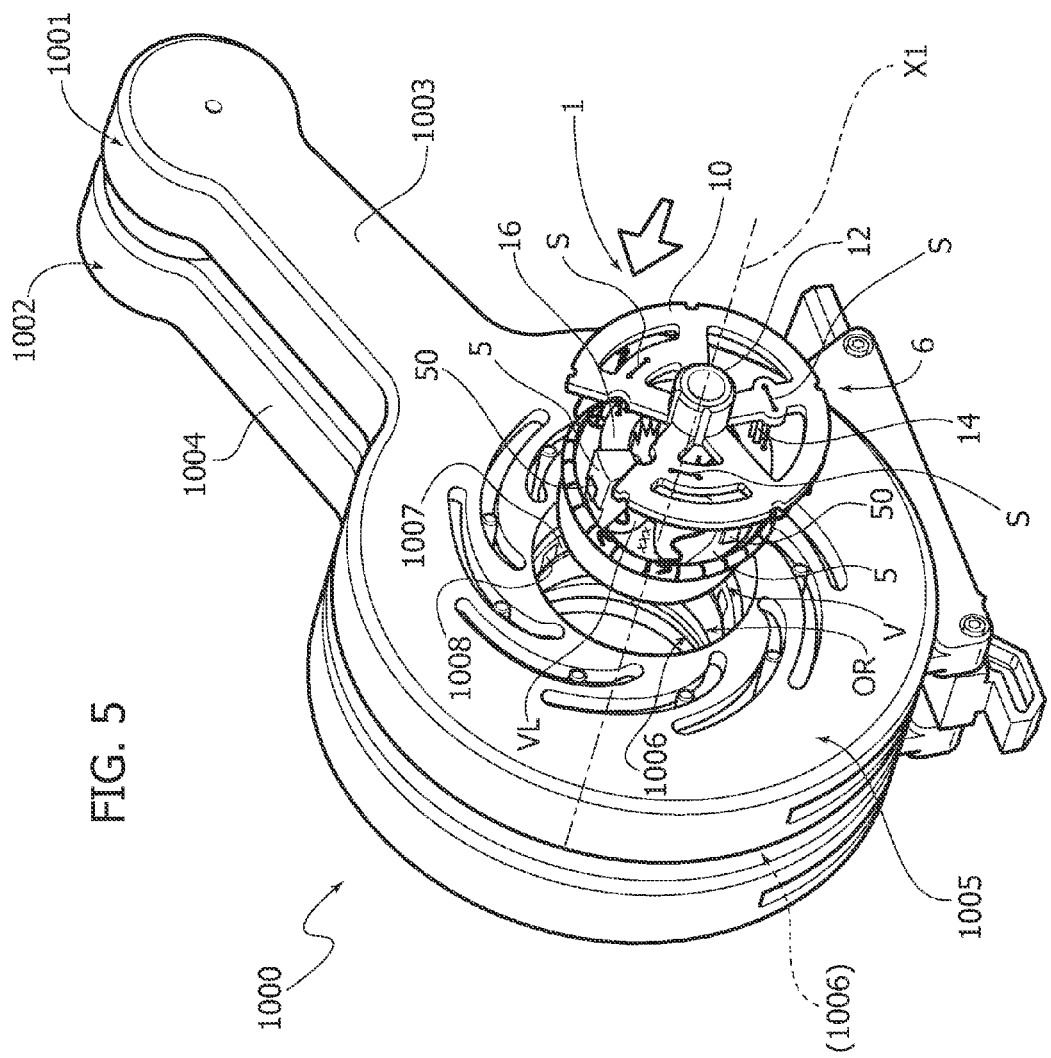
FIGS. 5, 6, 7, 8, and 9 illustrate an exemplary operative sequence which can be performed by using a kit according to various embodiments.

In certain embodiments, each array of crimping elements 1005, 1006 may include a plurality of crimping members in the form of blades (e.g., more or less like the diaphragm of a SLR camera) which define a radially contractible (i.e., having a variable diameter) crimping opening OR and are adapted to exert a radial contraction action on the radially contractible portion(s) of an implantable medical device (e.g., the prosthesis 4). In certain embodiments, such crimping elements may be in the form of wire-like elements (see. e.g., various embodiments as disclosed in EP-A-2 014 257). The radially contractible crimping opening OR, as in FIG. 5, is configured to receive at least one radially contractible axial portion of an implantable medical device. Those of skill in the art will otherwise appreciate that the disclosure that follows may be applied irrespective of the structure of the crimping elements.

In the exemplary embodiments shown in the figures, each blade is guided by means of a pin into a respective spiral track provided on the body of each crimping unit. The arrays of crimping elements may be spaced axially with respect to one another so that they are positioned in correspondence with the annular end portions IF, OF of the prosthesis 4.

Each crimping unit 1001, 1002 may be provided with a central circular opening OR which is defined by a cylindrical inner wall of each of the crimping unit and the crimping apparatus furthermore includes an intermediate portion, indicated by the reference 1007 and located between the crimping units 1001, 1002, which together with the cylindrical inner walls of the latter forms a receptacle for housing an implantable medical device for the crimping operation. On the intermediate portion 1007, for instance on the inner cylindrical surface thereof, there may be provided angular indicia 1008 which in certain embodiments may be shaped as a receptacle for the corresponding angular indicia 50 provided on the finger formations 5.

With reference again to FIG. 5, in a first step of an operative procedure for coupling an implantable medical device to a crimping apparatus, a kit 1 including a holder member 2, a support member 6 coupled (releasably) to the holder member 2, and an implant device such as the heart valve prosthesis 4 may be extracted from the jar J by the aid of the hub 12, which may facilitate the manipulation of the kit 1 by a practitioner.

The kit 1 may then be axially aligned with the crimping opening OR of the crimping apparatus 1000 and axially advanced into receptacle defined by the cylindrical inner walls of the crimping units 1001, 1002 and of the intermediate portion 1007. At this stage, the angular positioning of the prosthesis 4 with respect to the crimping opening OR does not need to be observed carefully, which may result in a reduction of the time required for performing the whole set of operations considered.

Figure 6:
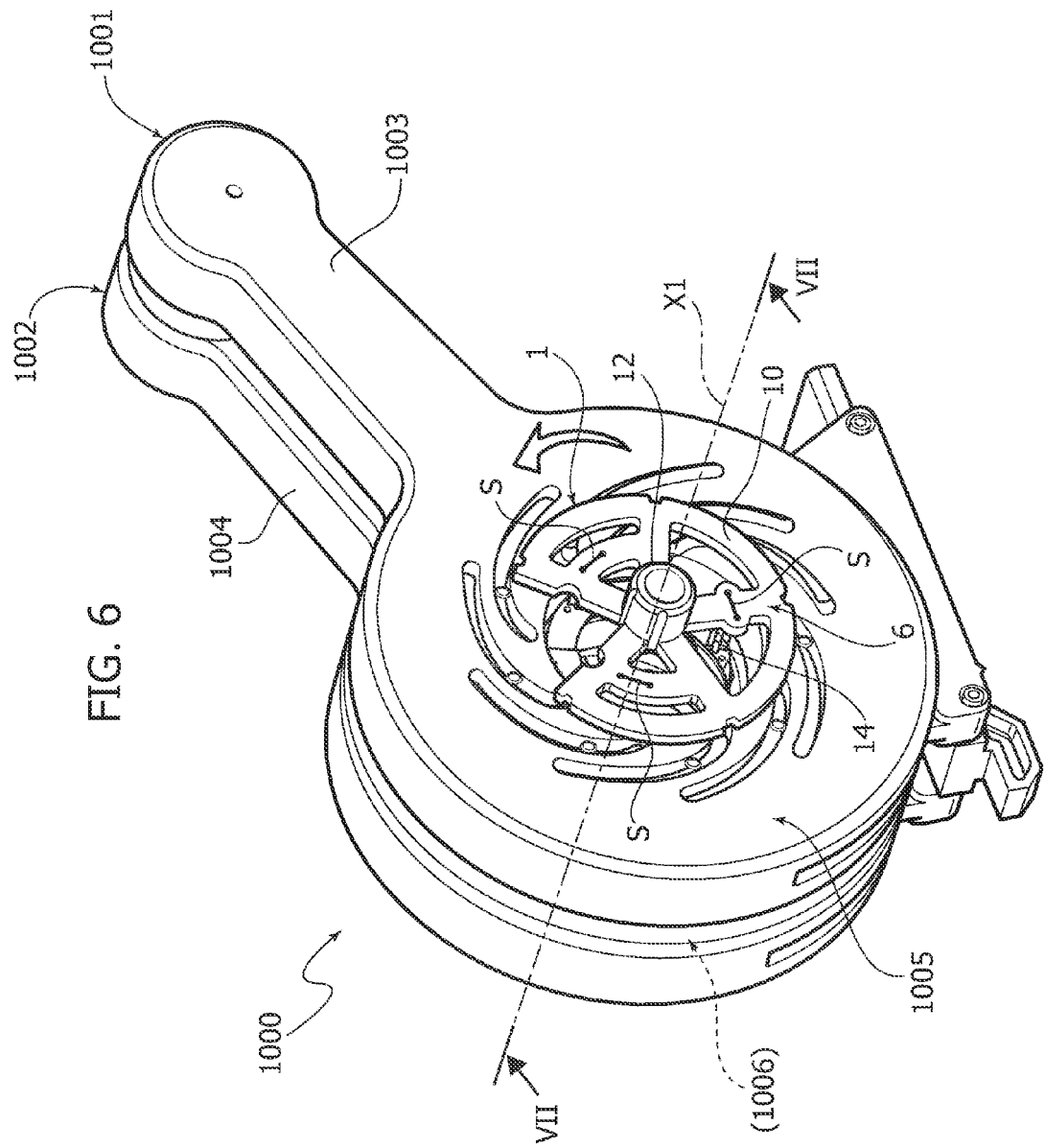

With reference to FIG. 6, in various embodiments, the axial advancement of the kit 1 through the crimping opening OR may be limited by the disc-shaped member 10, which is shaped so to have a diameter larger than both the crimping opening OR and the receptacle defined by the cylindrical inner walls of the crimping units 1001, 1002 and of the intermediate portion 1007. To this end, the axial length of the bridge elements 14 may be chosen so that when the disc member 10 comes axially into contact with the crimping apparatus, the heart valve prosthesis 4 has reached a desired axial position relative to the crimping units.

Figure 7:
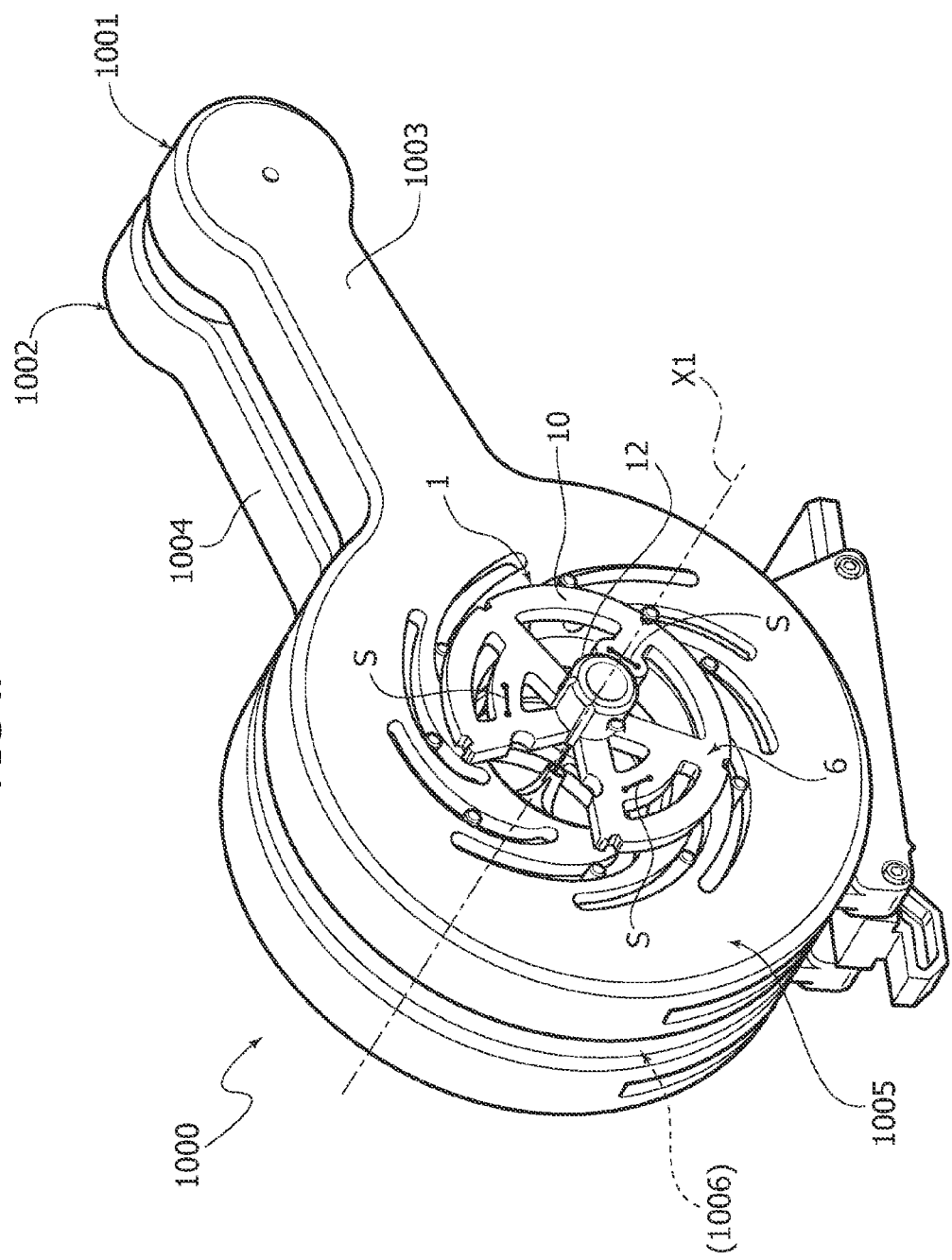

With reference to FIGS. 6 and 7, the holder member 2 is then rotated by imparting a rotary motion (around the axis X1) to the support member 6, optionally acting on the hub 12, until the angular indicia 50 (disposed on the fingers 5) engage with a corresponding angular indicia 1008 provided on the intermediate portion 1007 of the crimping apparatus. In certain embodiments, the crimping unit may include visible indicia corresponding to the angular indicia 1008 to allow the practitioner to identify, e.g., features of the prosthesis. In exemplary embodiments, engagement between the angular indicia may occur in a snap-fit fashion. A desired angular positioning of the prosthesis 4 may thus be easy to recognize due to the mechanical or tactile feedback provided to the practitioner by a snap fit engagement (and the clicking sound possibly associated therewith).

Figure 8:
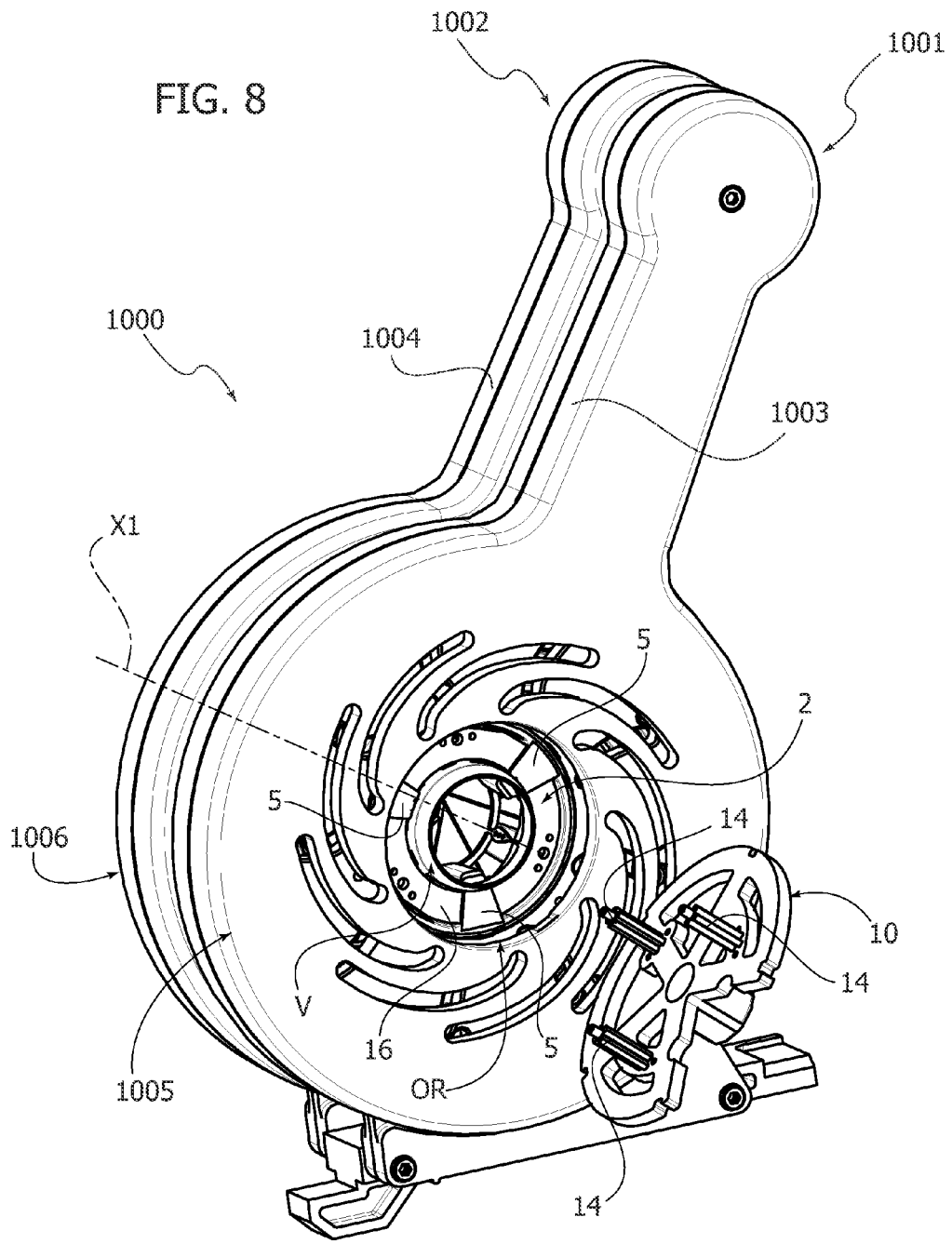

At this stage, which is represented in the cross-sectional view of FIG. 7A, an effective crimping action may not be exerted on the prosthesis 4 since the bridge elements 14 do not permit the crimping opening to shrink (i.e., to undergo a diameter reduction). Thus, in a next step, the suture threads S holding together the holder member 2 and the support member 6 may be cut by the practitioner so that the support member 6 (including the bridge elements 14) may be uncoupled from the holder member 2 and moved away from the crimping apparatus 1000 (FIG. 8).

In certain embodiments, as previously described, where the support member 6 may be integral with the holder member 2, the cross-section of the connection portions linking the support member 6 to the holder member 2 (e.g., such connection formations may be terminal axial portions of the bridge members 14) may be chosen so that a controlled collapse thereof occurs. In other words, in certain embodiments, the cross-section may be such that until the kit 1 is rotated to drive the angular indicia 50, 1008 into engagement with each other, the connection formations 40 are capable of withstanding the shear stresses that arise, but once engagement with the angular indicia is achieved, the connection portions 40 are no longer capable of withstanding the shear stresses that arise from a further rotation aimed at disengaging the angular indicia.

Figure 9:
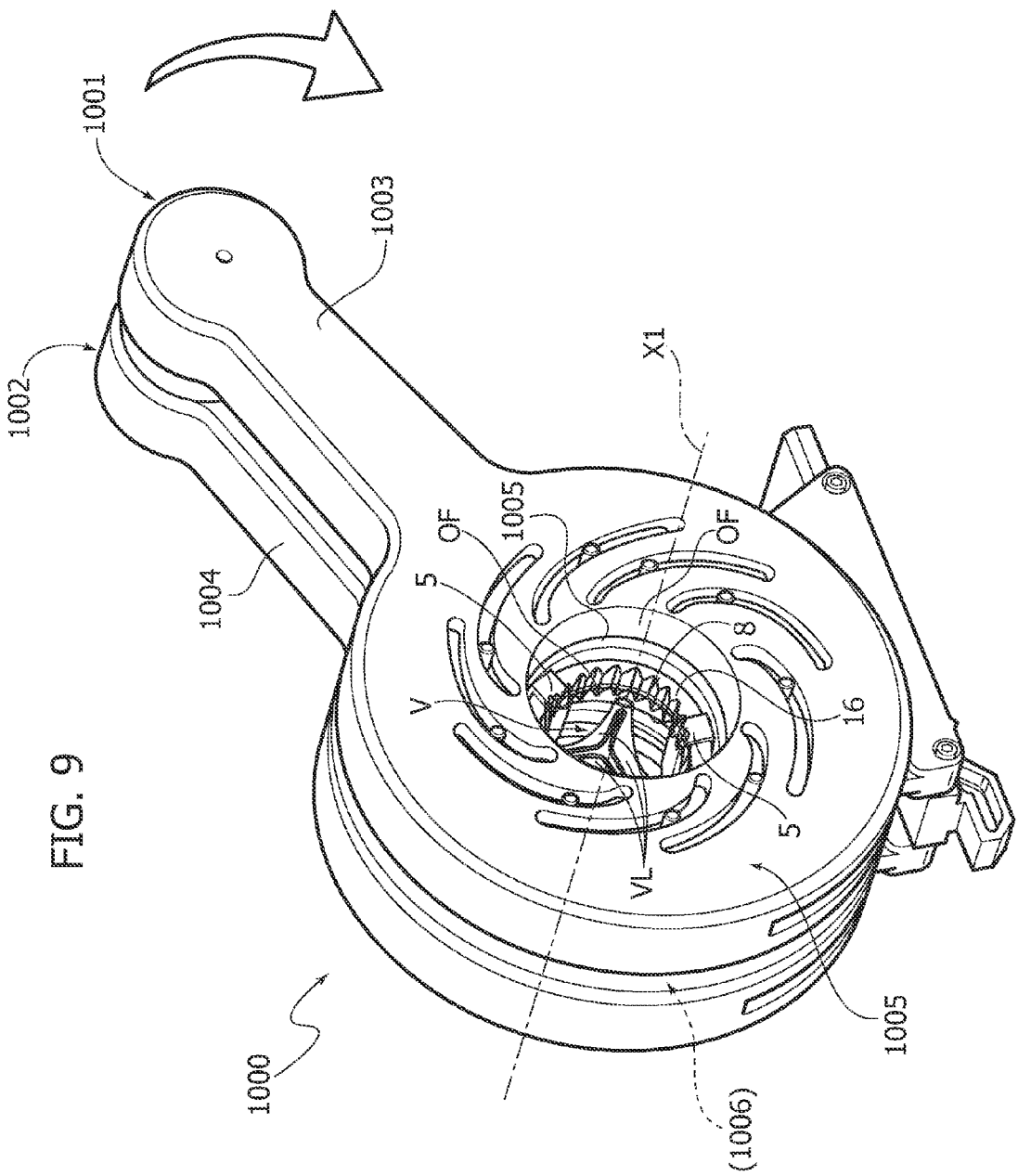

In various embodiments, as exemplified by FIGS. 7A and 9, irrespective of the type of coupling of the holder member 2 to the support member 6, while positioned within the crimping apparatus 1000, the holder member 2 will not hinder the action of the crimping units 1001, 1002 and the respective crimping elements. In various embodiments, the holder member 2 will support the prosthesis 4 from outside the tubular structure thereof and extend axially of the tubular structure of the prosthesis 4 at least in part axially clear of the radially contractible annular portion OF so that an unimpeded radial contraction of the radially contractible portions OF is permitted. This may be achieved, e.g., by providing the ring member 16 with an axial thickness which is less than the axial extension of the portion OF so that at least a distal end thereof (distal being used herewith reference to the implantation site) is left uncovered. In various embodiments, the ring member 16 is disposed somewhat axially below (i.e., in the direction toward or proximal the implantation site), such that the contractible annular portion OF is left completely uncovered by the ring member 16. In one exemplary embodiment, the ring member 16 is located about 0.1 to about 3 millimeters below (or proximal) the contractible annular portion OF.

In certain embodiments, as shown, the axial portion OF may not be covered by the holder member 2. Depending on the specific needs, a different arrangement may be devised, e.g., with the inflow portion IF, instead of the outflow portion OF, being enclosed within the ring member 16. In certain embodiments, the holder member 2 may have a closed cage structure with a pair of ring members 16 and finger formations extending therebetween, wherein each ring member 16 encloses a corresponding axial portion IF, OF. By way of example, in certain embodiments, the holder member 2 may be configured such that the ring member 16 leaves both the portions IF, OF axially uncovered. In various embodiments, the holder member 2 may be sized and dimensioned to be axially shorter than the axial distance between the two arrays of crimping elements 1005, 1006.

Further to the step considered in the foregoing, the actuating levers 1003, 1004 of the crimping apparatus 1000 may be rotated as shown in FIG. 8 in order to crimp the portions IF, OF (and the prosthesis 4 as a whole) onto a delivery instrument (not shown). While performing such operation, the axial connection formations 40 may be disengaged in a radial direction from the finger formations 5. In various embodiments, the finger formations 5 may be coated with (or made from) a low friction material so that the disengagement of the connection formations 40 may occur very smoothly. In various embodiments, before rotating the levers 1003, 1004 the delivery instrument is axially advanced through the ring support member and the first diameter orifice of the crimping apparatus, such that it may be coupled to the inflow portion IF and/or the outflow portion OF upon completion of the crimping action.

Various embodiments, as considered herein, offer considerable advantages over the prior art. The kit 1 offers fast, reliable and accurate performance. In various embodiments, the whole pre-operative procedure leading to crimping a medical device onto a delivery instrument can be completed without the practitioner having to directly contact the valve prosthesis with his or her own hands, which minimizes the risk of possible damage to the medical device. In various embodiments, after opening the jar J, the personnel inside the operational theatre may be simply required to take the kit 1 from the jar, place the kit within the crimping opening OR, rotate the kit until a desired angular position has been reached, cut the sutured threads, and separate the manipulation portion from the rest of the kit. Such operations require little time to be completed and result in the medical device being ready for crimping. In the various embodiments, the holder member 2 (together with the supporting portion 6) and the implantable medical device 4 may be pre-mounted and provide a simple and reliable facility for ensuring a correct positioning of a medical device within a crimping opening, without requiring that the medical device should be directly touched by hand.

Without prejudice to the underlying principles of the invention, the details and embodiments may vary, even significantly, with respect to what has been described herein, merely by way of example, without departing from the scope of the invention as defined by the annexed claims. Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

Figure 10:
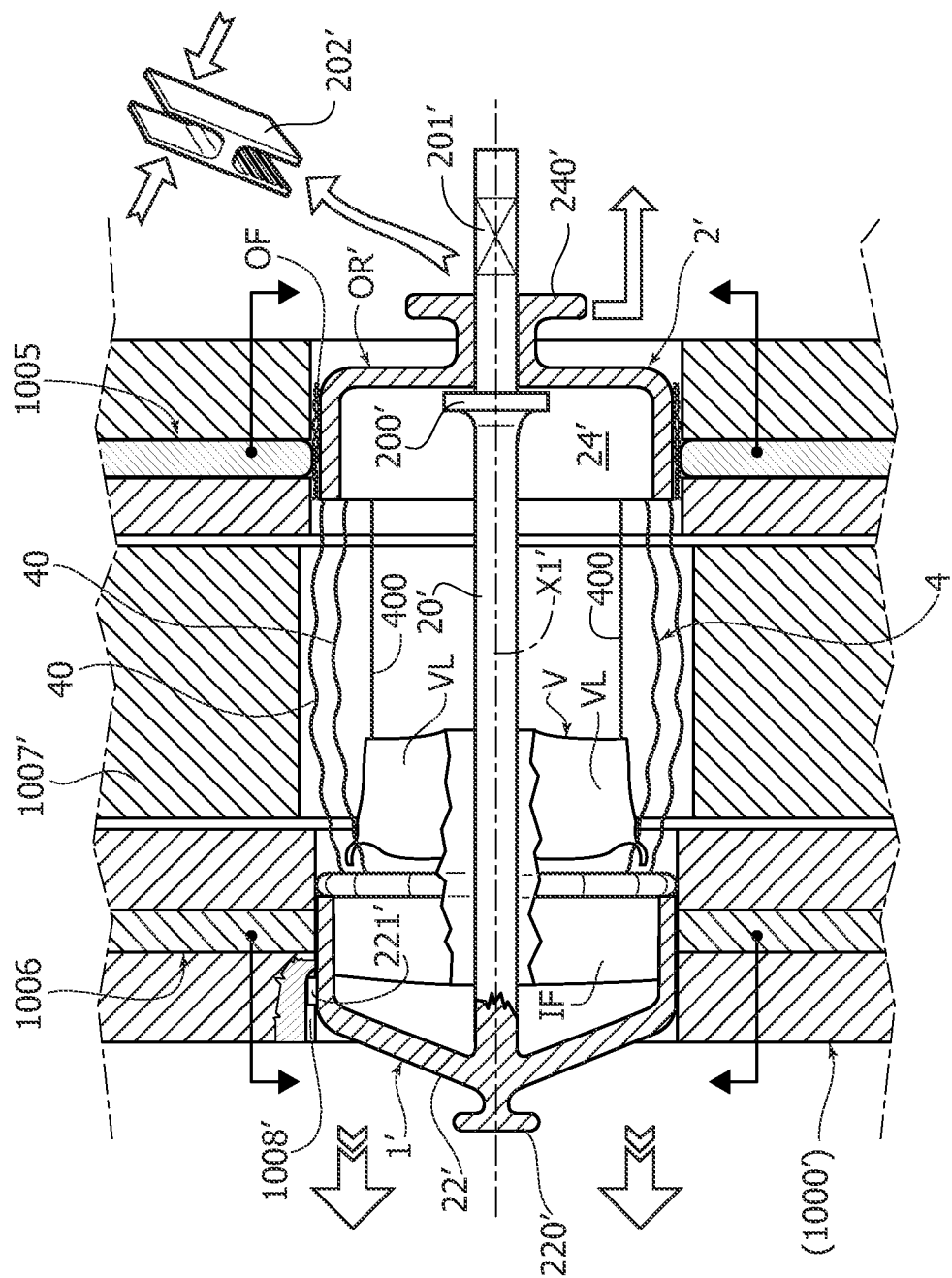
FIG. 10 is a cross-sectional view taken along axis X1 of FIG. 9 and substantially corresponding to that of FIG. 9 but showing a stage of an exemplary operative sequence which can be performed by using a further embodiment of a kit.

With reference furthermore to FIG. 10, a kit according to further embodiments is designated as a whole by the reference 1' and is depicted inserted in a crimping apparatus 1000'. In various embodiments, the kit 1' includes a holder member 2' supporting an implantable medical device, e.g., the medical device 4, wherein the holder member 2' extends axially of the tubular structure of the implantable medical device 4. Similarly to the kit 1, the kit 1' may be configured for being stored in a jar J. In various embodiments, the holder member 2' includes a shaft 20', a first support member 22' connected to the shaft 20' (or even integrally formed therewith, in some embodiments) and a second support member 24' slidably mounted on the shaft 20'. All the above mentioned components are coaxial to an axis X1', which also coincides with a central axis of the implantable medical device 4.

In various embodiments, the first support member 22' may be configured as a cap supporting the implantable medical device 4 from outside the tubular structure thereof. In certain embodiments, wherein the medical device 4 is the sutureless aortic valve prosthesis described in the previous paragraphs, the first support member 22' may be configured for supporting the inflow axial portion IF (from outside). In such embodiments, one or more angular indicia 221' may be provided on an external surface of the support member 22'. Such angular indicia may be, for example, in the form of radially protruding tabs or reliefs.

In various embodiments, the second support member 24' may, instead, be configured as a hub supporting the medical device 4 from inside the tubular structure thereof. In the embodiments in which the medical device 4 is the sutureless aortic valve prosthesis described in the previous paragraphs, the second support member 24' may be configured for supporting the outflow axial portion OF.

In certain embodiments, advantageously, a combination of a stop member 200', for example in the form of a collar, and a flattened portion 201' whereon a removable locking member 202' engages may be provided in order to ensure a proper relative positioning of the two support members 22', 24'. Furthermore, in various embodiments each of the support members 22', 24' may be provided with an end flange 200', 240', respectively, which facilitates the manipulation thereof. More particularly, the two support members 22' and 24' may be kept at a distance, for example, by means of the stop member 200', which may be used to set the minimum axial distance between them. The axial movement of the support member 24' may be further restricted by means of the removable locking member 202'. In this way, one may ensure that no undesired displacement of the support elements will occur.

As shown in FIG. 10, the shaft 20' extends through the device 4 and may terminate with a handle (not shown) which allows one to manipulate the kit. Such a handle may conveniently be provided as a separate part to be coupled to the kit 1', prior to extracting the latter from the jar J.

The crimping apparatus 1000' is similar to the apparatus 1000, except that angular indicia 1008' are provided on an internal cylindrical surface of the crimping opening OR' at a position substantially corresponding to one of the two arrays of crimping elements 1006 or 1005. Moreover, in various embodiments, the angular indicia 1008' may be provided, e.g., as axial grooves.

An exemplary operative sequence that may be performed by using the kit 1' may be summarized as follows. The kit 1' is extracted from the jar J (not shown in FIG. 10 but similar to that depicted in FIG. 1 in phantom line) and—if required—a handle is coupled to the shaft 20. The kit 1' is then advanced axially into the crimping opening OR' until a desired axial position has been reached. To this end, visible axial indicia may be provided on either (or both) of the support members 22', 24' or, for example, the end flange 240' itself may be shaped so to offer an axial reference. This may be achieved, for example, by providing one or more radially protruding tabs projecting radially by a distance sufficient to exceed the radius of the crimping opening (in this way, the end flange 240' may assume—so to say—a "propeller-like" shape). In other embodiments, one may also envisage to choose the diameter of the end flange 240' so that it is larger than that of the crimping opening OR'. The kit 1 may then be rotated until each of the angular indicia 221' engage into a corresponding groove 1008', e.g., in a snap-fit fashion. In this way, a correct angular positioning of the prosthesis 4 may be achieved. Next, the removable locking member 202' may be removed (in the example shown in FIG. 10, such member is provided as a clip), so that each of the support members 22', 24' may be disengaged axially from the prosthesis 4, although in opposite directions. To this end, the practitioner may rely upon the end flanges 220', 240' in order to grasp each supporting member and drive it out of the crimping apparatus. The prosthesis 4 is now ready to be crimped.

Figure 11:
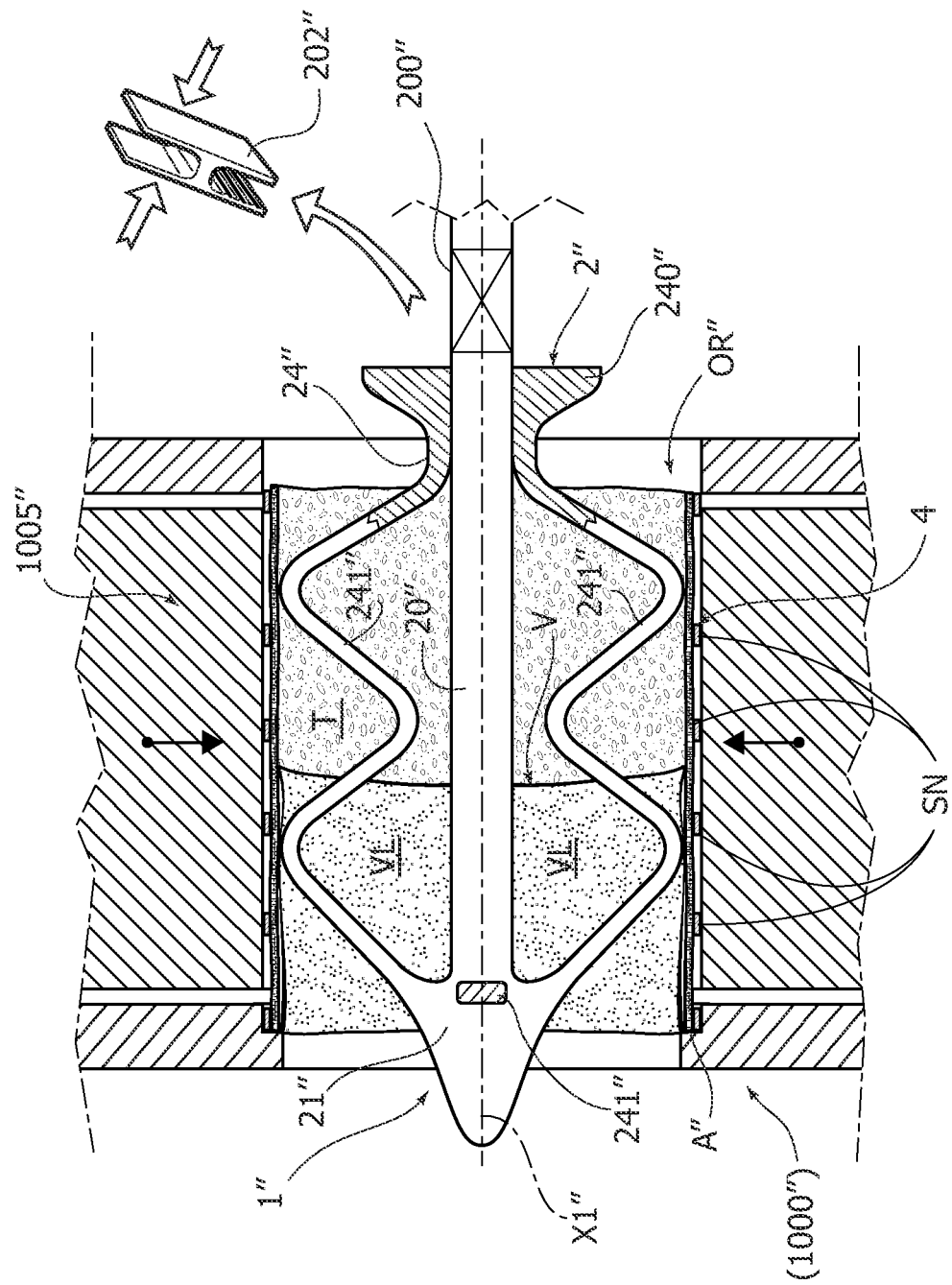
FIGS. 11 and 12 are cross-sectional views again taken along axis X1 of FIG. 9 (and indicated as axis X1' in the Figures) and substantially corresponding to that of FIG. 9, but showing a stage of an exemplary operative sequence which can be performed by using yet a further embodiment of a kit.
Figure 12:
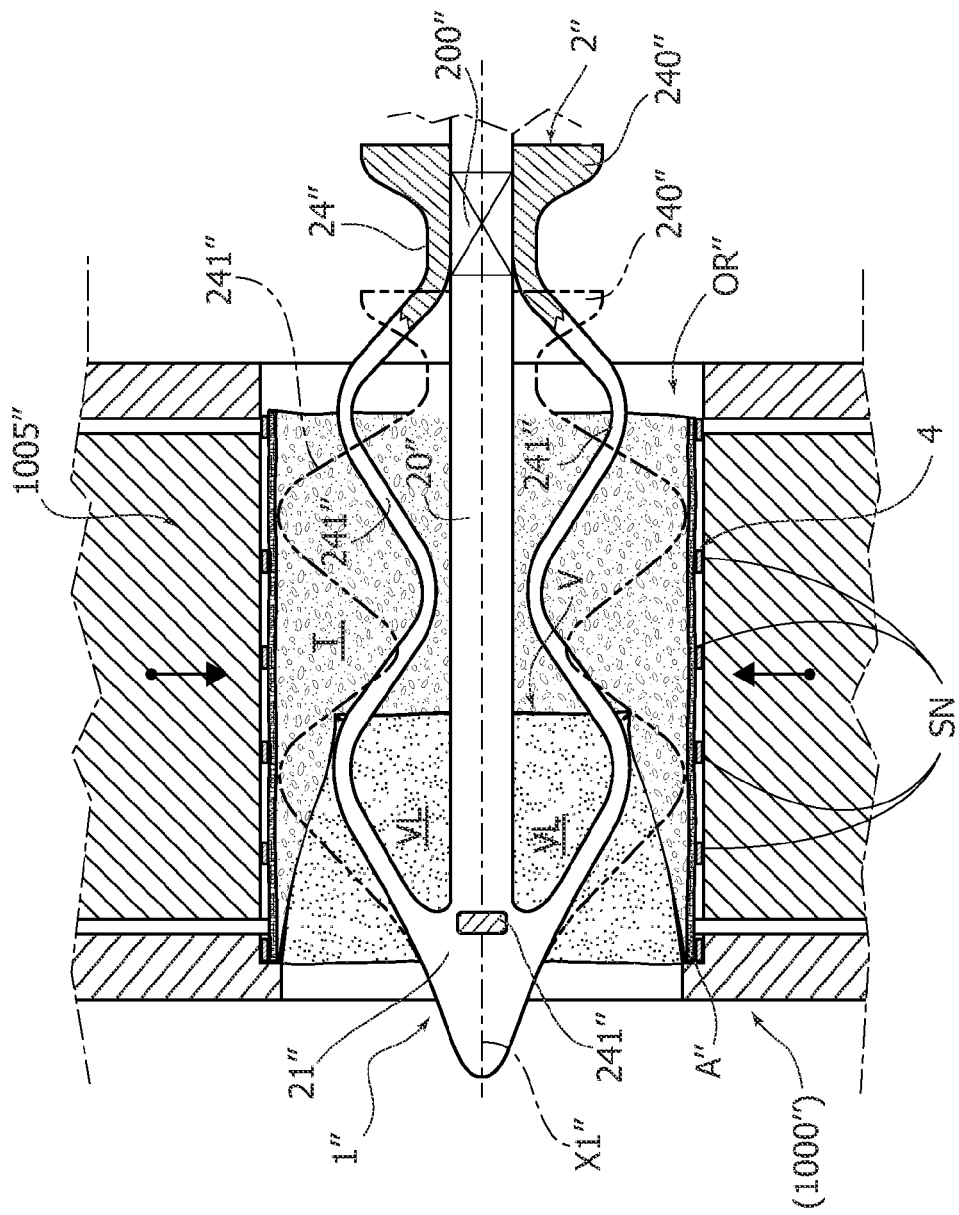

With reference now to FIGS. 11 and 12, yet a further embodiment of a kit, according to the invention, is designated as a whole by the reference 1'. In various embodiments, the kit 1" includes a holder member 2" supporting an implantable medical device, e.g., the medical device 4, wherein the holder member 2" extends axially—along an axis X1"—of the tubular structure of the implantable medical device 4. Similarly to the kit 1, the kit 1" may be configured for being stored in a jar J. In the examples depicted in the figures, the implantable medical device is configured as a stented heart valve prosthesis including a stent armature SN, a tissue sheath T applied within the stent armature SN and a biological valve V including a plurality of valve leaflets VL.

In various embodiments, the holder member 2" may include a shaft 20" terminating in a nosecone 21" wherefrom a plurality of elastic, deformable, preferably wave-shaped (e.g., sinusoidal), and axially extending arms 241" depart. Such arms 241" re-join at a slidable hub 24',' provided with an end flange 240" and slidably mounted on the shaft 20". The shaft 20" furthermore may include a flattened portion 200" whereon a removable locking member—for example, in form of a clip 202"—may be fitted, thereby limiting the axial displacement of the hub 24". The arms 241" constitute supporting formations configured for supporting the medical device 4 from inside the tubular structure thereof; in particular, with reference to FIG. 11. Such, such coupling may be achieved by establishing a slight interference with the tubular structure of the valve in the undeformed condition of the arms 241", i.e., that shown in FIG. 11.

An exemplary operative sequence which can be performed by using the kit 1" may be as follows. The kit 1" is extracted from the jar J and it is inserted axially into the crimping opening OR" of a crimping apparatus 1000". Such a crimping apparatus may include, in the example shown in the figures, a single array of crimping elements 1005" providing radial contraction of a crimping opening OR". The insertion of the kit 1" into the apparatus 1000" is preferably performed by having the nosecone 21" ahead in the direction of advancement. Once the desired axial positioning has been reached, for example, by means of an axial abutment surface A", the removable locking member 202" is removed from the flattened portion 200" of the shaft 20", so that the hub 24" may be slid distally away from the nosecone 21" and the prosthesis 4. The sliding of the hub 24"results in an elongation of the arms 241" and at the same time in a radial contraction thereof, so that the holder member 2" becomes loose with respect to the prosthesis 4. It is, therefore, possible to disengage the holder member 2 from the prosthesis 4 and remove it completely from the crimping opening OR". The prosthesis 4 can now be crimped and coupled to a delivery tool (not shown).

Figure 13:
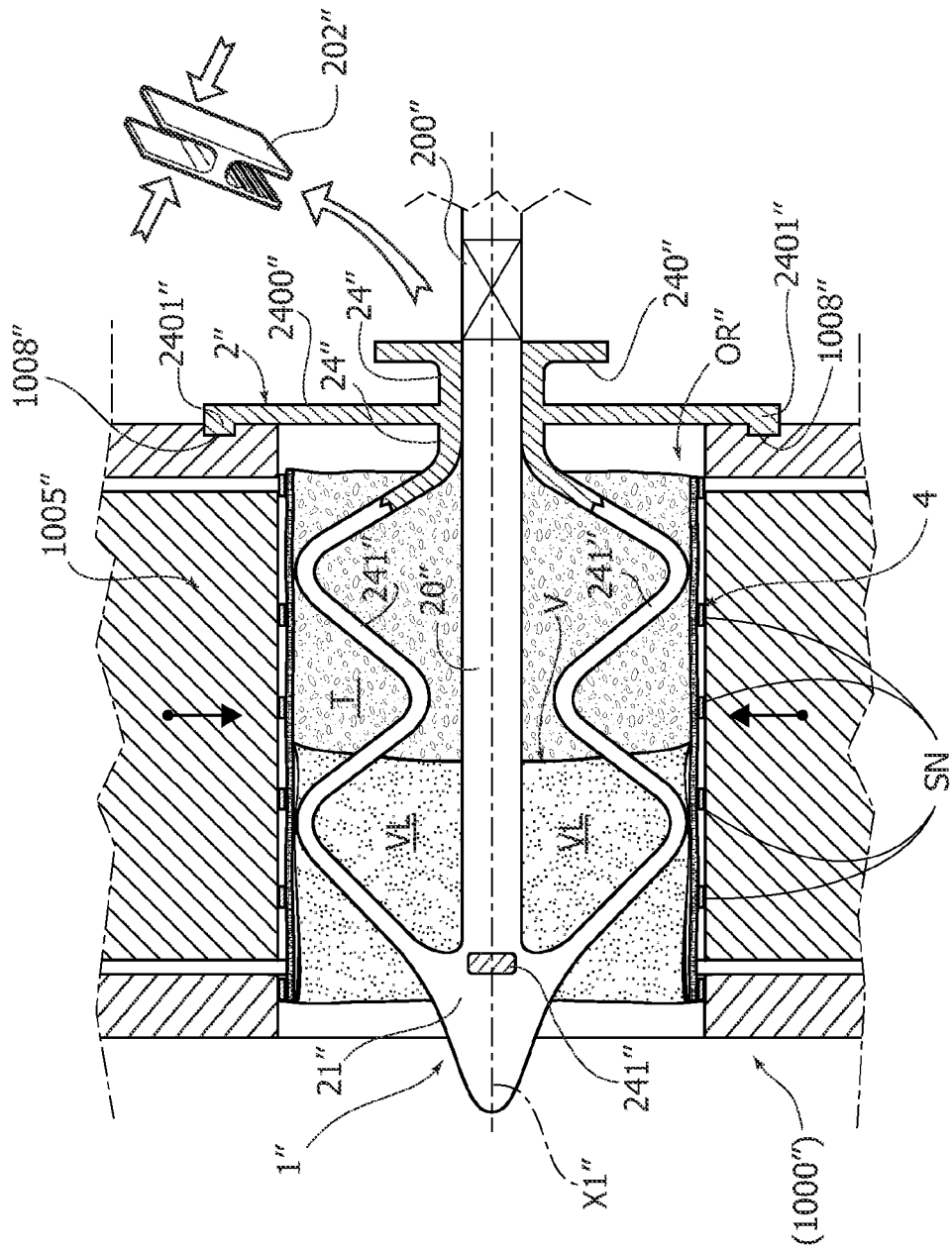
FIGS. 13 and 14 correspond to FIGS. 11 and 12 and depict a variant of the embodiment illustrated therein.
Figure 14:
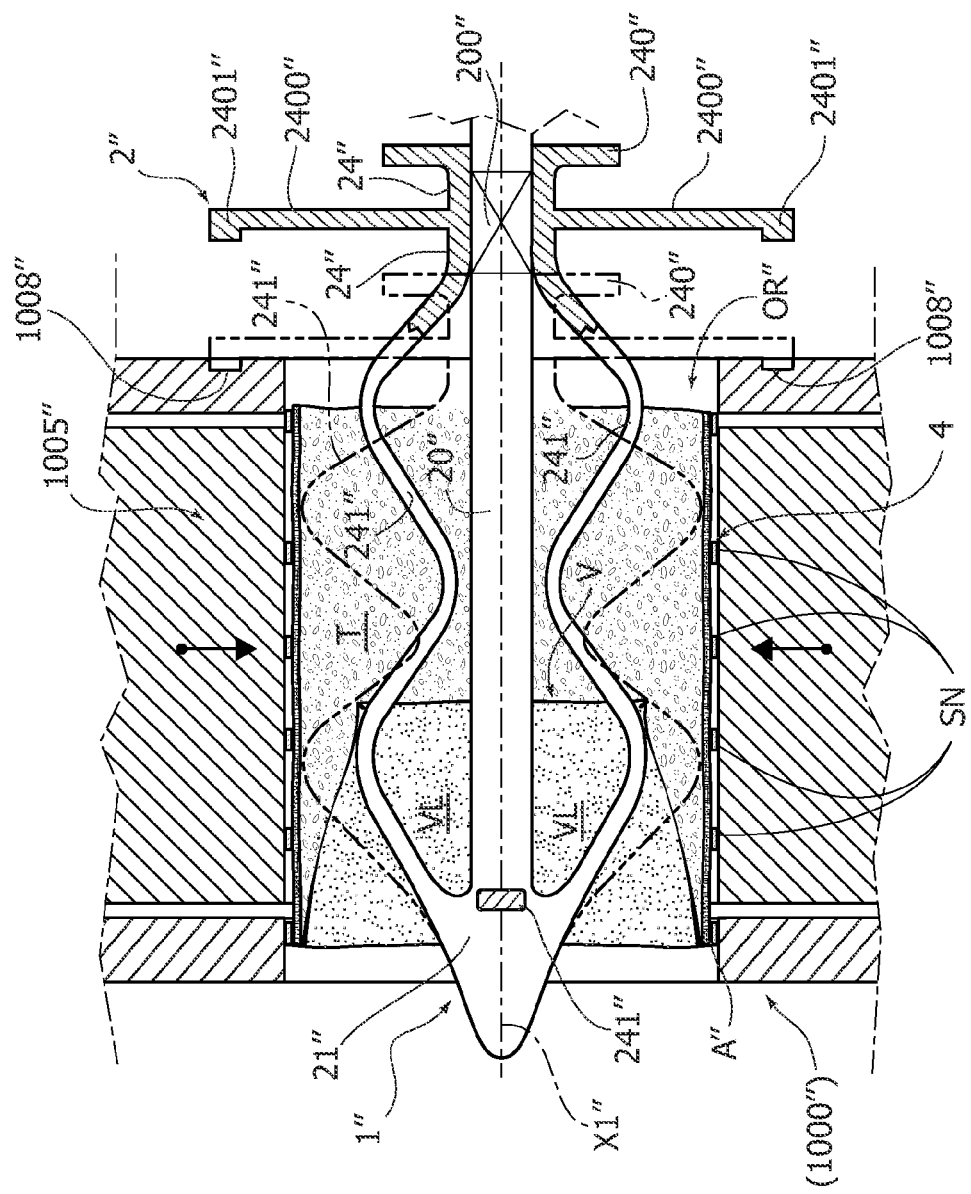

In some embodiments, such as those depicted in FIGS. 13 and 14, both an axial and radial positioning of the prosthesis 4 may be achieved. On the hub 24", in addition to the end flange 240", there may be provided a plurality of radial arms 2400" (e.g., in the number of three), each provided in turn with an axial protrusion 2401". Such axial protrusions 2401" may be configured for acting as angular indicia and furthermore for engagement with corresponding angular indicia 1008" provided on a front surface of the crimping apparatus 1000". To this end, in various embodiments, the extension in radial direction of each of the arms 2400" is chosen so to be greater than the radius of the crimping opening OR".

The operating sequence develops substantially in the same way as previously described, except that the axial positioning of the prosthesis is now provided by the contact between the arms 2400" and the crimping apparatus. Furthermore, once the desired axial positioning has been reached, the kit 1" may be rotated by acting on the holder member 2 until the axial protrusions 2401" engage into the corresponding angular indicia 1008", e.g., in a snap-fit manner. In such embodiment, the axial abutment surface A" may not be present, as the axial reference may be provided only by the arms 2400". After the desired angular position has been achieved, the removable locking member may be disengaged from the shaft 20", so that the hub 24" can be slid away from the prosthesis 4, thereby enabling the disengagement of the holder member 2" from the prosthesis 4. Note that it is also possible to have the axial protrusions 2401" provided on a disc-shaped structure formed as a flange on the hub 24", instead of the arms 2400".

Figure 15:
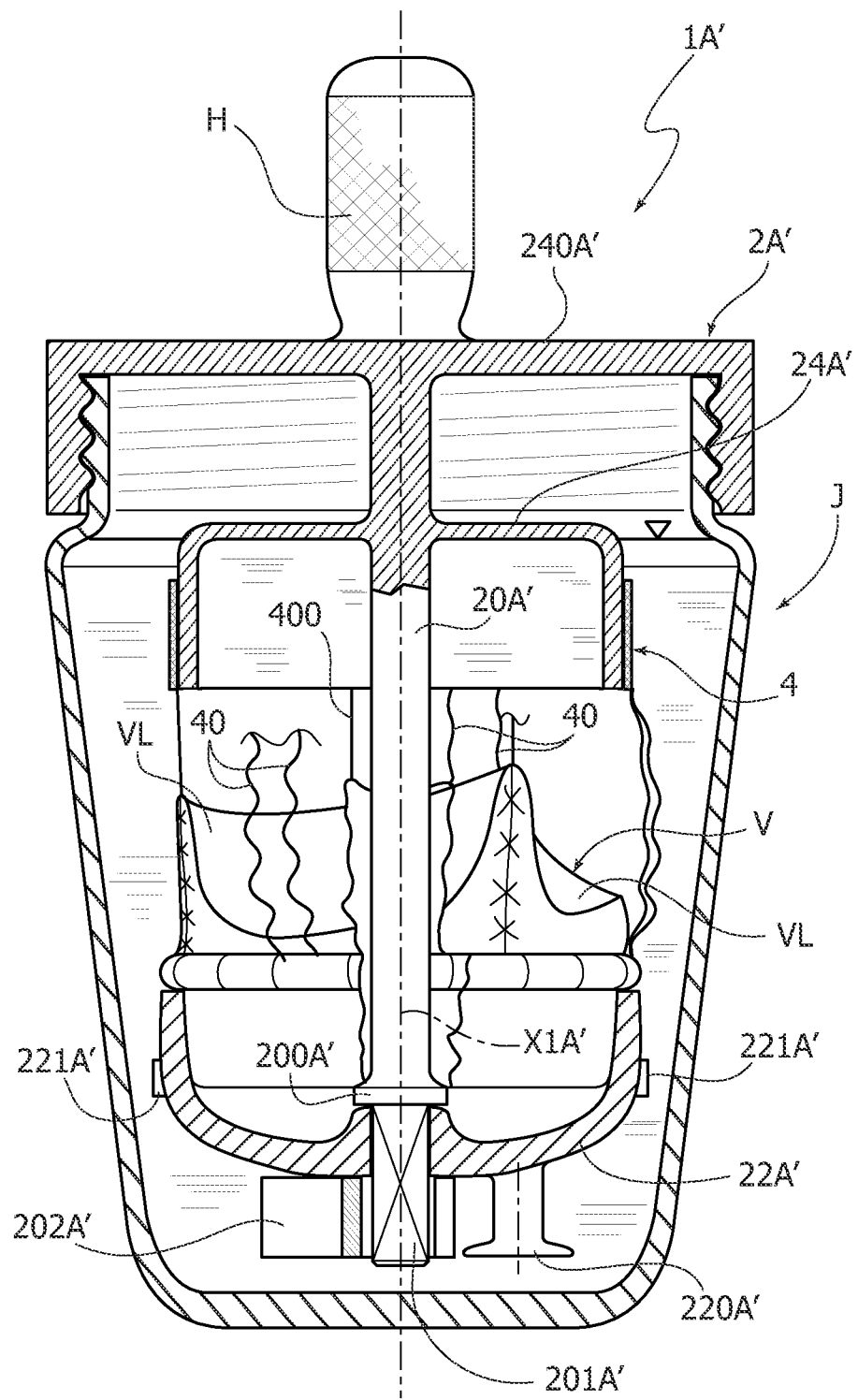
FIG. 15 is a cross-sectional view showing yet a further embodiment of a kit.

With reference now to FIG. 15, a further embodiment of the kit 1' is designated as a whole by the reference 1A'. In various embodiments, the kit 1A' includes a holder member 2A' supporting an implantable medical device, e.g., the medical device 4, wherein the holder member 2A' extends axially of the tubular structure of the implantable medical device 4. The kit 1A', is configured for being stored in a jar J. In the example shown in the figures, the kit 1A' is depicted immersed in a liquid contained within a jar J. Such a liquid may be a liquid beneficial to the integrity of the valve leaflets VL of the prosthesis 4 or, should a polymeric prosthetic valve be used in the prosthesis 4, a liquid intended to preserve the sterility of the polymeric leaflets.

In various embodiments, the holder member 2' includes a shaft 20A', a first support member 22A' slidably mounted on a flattened, preferably squared, section 201A' of the shaft 20' and a second support member 24' connected to the shaft 20', e.g., rigidly connected thereto or integral therewith. The first support member 22A' may be temporarily held in place by the joint action of a collar member 200A' on a first side thereof and of a removable locking member 202A' (e.g., a clip) engaged on the flattened section 201A' on the other side. Furthermore, in various embodiments, the shaft 20A' is connected to (e.g., rigidly connected) or integral with a cap 240A' of the jar J. The cap 240A' may act as an end flange and facilitate the manipulation of the kit 1A'. Additionally, in such embodiments, the cap 240 may be provided with a handle H, which may be integrally formed therewith. In other embodiments, the handle H is not present. All the components mentioned above are coaxial to an axis X1A', which also coincides with a central axis of the implantable medical device 4.

In various embodiments, the first support member 22' may be configured as a cap supporting the implantable medical device 4 from outside the tubular structure thereof. In certain embodiments, wherein the medical device 4 is the sutureless aortic valve prosthesis described in the previous paragraphs, the first support member 22' may be configured for supporting the inflow axial portion IF (from outside). In such embodiments, one or more angular indicia 221A' may be provided on an external surface of the support member 22A'. Such angular indicia 221A' may be, for example, in the form of radially protruding tabs or reliefs. Additionally, a pin provided with an end flange 220A' may be provided on the member 22A' on an end surface thereof. In various embodiments, the second support member 24A' may, instead, be configured as a hub supporting the medical device 4 from inside the tubular structure thereof. In the embodiments, wherein the medical device 4 is in the sutureless aortic valve prosthesis described in the previous paragraphs, the second support member 24' may be configured for supporting the outflow axial portion OF.

An exemplary operative sequence that may be performed by using the kit 1A' may be summarized as follows and, generally, may be quite similar to the sequence described with reference to the kit 1'. The implantable medical device 4 is extracted from the jar J supported by the holder member 2A' simply by unscrewing the cap 240 from the jar J itself (thereby, unscrewing the entire kit 1A' therefrom). The kit 1' may be then advanced axially into the crimping opening OR' of the apparatus 1000' previously described until a predetermined axial position has been reached. To this end, the cap 240, which is generally dimensioned so that the external diameter thereof is larger than the diameter of the crimping opening OR', may act as an end-of-travel element by coming into contact with a front surface of the crimping apparatus 1000'. The axial distance between the second support member 24A' and the first support member 22A' is chosen so to have the axial portions supported by the support members 22A', 24A' placed in correspondence of the arrays of crimping elements 1005', 1006' when the cap 240 comes into contact with the crimping apparatus 1000'. The radial positioning of the medical device 4 may be effected in the same manner as described previously within. The removable locking member 201A' may then be removed from the shaft 20A' so that the first support member 22A' may be slid axially away from the crimping opening OR' and from the kit 1A'. Afterwards, on the opposite side, the remainder of the holder member 2A' can be removed from the crimping opening OR', again in an axial, yet opposite, direction. The medical device 4 is now ready to be crimped.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A kit for facilitating crimping of a prosthetic heart valve for implantation at an aortic valve site in a human heart, the aortic valve site including a plurality of valve sinuses, the kit comprising:
   a prosthetic aortic heart valve having a tubular structure and a first central axis including:
      an anchoring structure comprising an annular outflow member, an annular inflow member, and a plurality of axial connection formations that connect the annular outflow member and the annular inflow member, wherein the axial connection formations are arranged in pairs angularly distributed around the central axis, and the axial connection formations bulge outward to provide anchoring at the valve site;
      a plurality of leaflets coupled to the anchoring structure and adapted to substantially allow blood flow in a first direction and to substantially prevent blood flow in a second direction;
      wherein the annular outflow member and the annular inflow member are radially contractible toward the central axis;
   a holder member supporting the prosthetic aortic heart valve, the holder member comprising:
      a first disc support member that includes a central hub and a plurality of bridge elements, wherein the hub and the bridge elements extend axially from opposite sides of the disc support member; and a second ring support member that includes receptacles for coupling with the bridge elements, and a plurality of finger formations protruding axially from the ring member and extending lengthwise along at least a portion of the prosthetic aortic heart valve, wherein the ring member surrounds the prosthetic aortic heart valve and is axially aligned at or slightly proximal to the annular outflow portion, wherein the plurality of finger formations are circumferentially spaced and sized to fit between the angularly distributed pairs of axial connection formations such that each pair of axial connection formations frictionally engages and thereby couples to a corresponding finger formation, and wherein the first disc support member and the second ring support member are releasably coupled by sutures.

2. The kit of claim 1, further comprising a container holding a liquid and having a cap, the container sized and shaped to hold the prosthetic aortic heart valve and the holder member such that the valve is immersed in the liquid and the hub of the holder member is connected to or integral with the cap.

3. The kit of claim 1, wherein the holder member includes a plurality of angular indicia to facilitate the holder member to be placed in a desired angular position with respect to a crimping opening of a crimping apparatus used to crimp the prosthetic aortic heart valve.

4. The kit of claim 1, wherein the prosthetic aortic heart valve includes an elastically biased tubular structure resisting radial contraction, and wherein the holder member supports the prosthetic aortic heart valve by radially constraining said elastically biased tubular structure.

5. A kit for facilitating crimping of a prosthetic heart valve for implantation at an aortic valve site in a human heart, the aortic valve site including a plurality of valve sinuses, the kit comprising:

a prosthetic aortic heart valve having a tubular structure and a first central axis including:

an anchoring structure comprising an annular outflow member, an annular inflow member, and a plurality of axial connection formations that connect the annular outflow member and the annular inflow member, wherein the axial connection formations are arranged in pairs angularly distributed around the central axis, and the axial connection formations bulge outward to provide anchoring at the valve site;

a plurality of leaflets coupled to the anchoring structure and adapted to substantially allow blood flow in a first direction and to substantially prevent blood flow in a second direction;

wherein the annular outflow member and the annular inflow member are radially contractible toward the central axis to permit crimping;

a holder member supporting the prosthetic aortic heart valve, the holder member comprising:

a first disc support member that includes a central hub and a plurality of bridge elements, wherein the hub and the bridge elements extend axially from opposite sides of the disc support member; and a second ring support member that includes receptacles for coupling with the bridge elements, and a plurality of finger formations protruding axially from the ring member and extending lengthwise along at least a portion of the prosthetic aortic heart valve, wherein the first disc support member and the second ring support member are releasably coupled.

6. The kit of claim 5, further comprising a container holding a liquid and having a cap, the container sized and shaped to hold the prosthetic aortic heart valve and the holder member such that the valve is immersed in the liquid and the hub of the holder member is connected to or integral with the cap.

7. The kit of claim 5, wherein the prosthetic aortic heart valve includes an elastically biased tubular structure resisting radial contraction, wherein said holder member supports the prosthetic aortic heart valve by radially constraining said elastically biased tubular structure.

8. The kit of claim 5, wherein the first and second support members of the holder member are releasably coupled by sutures.

9. The kit of claim 5, wherein the axial connection formations are arranged in angularly spaced pairs and the finger formations are sized and dimensioned to fit between the angularly spaced pairs of axial connection formations, such that the finger formations releasably couple to the axial connection formations.

10. The kit of claim 5, wherein the holder member includes angular indicia provided thereon in order for the holder member to be placed in a desired angular position with respect to a crimping opening of a crimping apparatus used to crimp the prosthetic aortic heart valve.

11. The kit of claim 5, wherein the second ring support member surrounds and supports the annular outflow portion of the prosthetic aortic heart valve.

12. The kit of claim 5, wherein the finger formations of the second ring support member extend axially a sufficient distance to surround and support the annular inflow portion of the prosthetic aortic heart valve.

13. The kit of claim 5, further comprising a crimping apparatus for crimping the prosthetic aortic heart valve, the crimping apparatus including a radially contractible crimping opening configured for receiving at least one radially contractible axial portion of the prosthetic aortic heart valve coupled to the holder, whereby a radial contraction of said crimping opening produces radial contraction of said at least one radially contractible axial portion of the prosthetic aortic heart valve.

14. The kit of claim 13 further comprising angular indicia provided on at least one of the crimping apparatus and the holder member to permit rotating the holder member supporting the prosthetic aortic heart valve to a given angular position with respect to the crimping opening of the crimping apparatus.

15. The kit of claim 13, wherein the finger formations of the holder include a first engagement feature adapted to couple with a second engagement feature on the crimping apparatus, such that the holder member is retained at a given angular position within the crimping apparatus.

16. A method of crimping a prosthetic aortic heart valve, the method comprising the steps of:

providing a crimping apparatus comprising a first annular body and a second annular body arranged for relative rotation generally about an axis, an array of linear crimping elements having first ends coupled to the second annular body, wherein the first body and the second body are configured to rotate about the axis between a first position, wherein the crimping elements define a first diameter orifice, and a second position, wherein the crimping elements define a second diameter orifice; and providing a kit comprising:
  a prosthetic aortic heart valve having a tubular structure and a first central axis including:
    an anchoring structure comprising an annular outflow member, an annular inflow member, and a plurality of axial connection formations that connect the annular outflow member and the annular inflow member, wherein the axial connection formations are arranged in pairs angularly distributed around the central axis, and the axial connection formations bulge outward to provide anchoring at a valve site;
    a plurality of leaflets coupled to the anchoring structure and adapted to substantially allow blood flow in a first direction and to substantially prevent blood flow in a second direction;
    wherein the annular outflow member and the annular inflow member are radially contractible toward the central axis to permit crimping;
  a holder member supporting the prosthetic aortic heart valve, the holder member comprising:
    a first disc support member that includes a central hub and a plurality of bridge elements, wherein the hub and the bridge elements extend axially from opposite sides of the disc support member; and
    a second ring support member that includes receptacles for coupling with the bridge elements, and a plurality of finger formations protruding axially from the ring member and extending lengthwise along at least a portion of the prosthetic aortic heart valve,
      wherein the finger formations include a first engagement feature for coupling with a second engagement feature on the crimping apparatus, and
      wherein the first disc support member and the second ring support member are releasably coupled;
axially advancing the holder into the first diameter orifice such that;
rotating the holder until the first and second engagement features engage;
cutting sutures coupling the first disc support member and the second ring support member;
removing the first disc support member from the crimping apparatus;
axially advancing a delivery device through the second ring support member and into first diameter orifice of the crimping apparatus;
rotating the first annular body and second annular body of the crimping apparatus to the second position in order to crimp the annular inflow portion and the annular outflow portion of the prosthetic heart valve; and
coupling at least one of the crimped annular inflow portion and the crimped annular outflow portion onto the delivery device.

* * * * *